US011826345B2

(12) United States Patent
Alkon

(10) Patent No.: US 11,826,345 B2
(45) Date of Patent: Nov. 28, 2023

(54) DOSING REGIMENS OF PKC ACTIVATORS

(71) Applicant: COGNITIVE RESEARCH ENTERPRISES, INC., Morgantown, WV (US)

(72) Inventor: Daniel L. Alkon, Chevy Chase, MD (US)

(73) Assignee: Synaptogenix, Inc., New York, NY (US)

( * ) Notice: Subject to any disclaimer, the term of this patent is extended or adjusted under 35 U.S.C. 154(b) by 381 days.

(21) Appl. No.: 17/060,541

(22) Filed: Oct. 1, 2020

(65) Prior Publication Data
US 2021/0023048 A1 Jan. 28, 2021

Related U.S. Application Data

(63) Continuation of application No. 16/513,058, filed on Jul. 16, 2019, now Pat. No. 11,173,140, which is a continuation of application No. 15/766,642, filed as application No. PCT/US2016/056201 on Oct. 8, 2016, now abandoned.

(60) Provisional application No. 62/238,952, filed on Oct. 8, 2015.

(51) Int. Cl.
| | | |
|---|---|---|
| *A61K 31/366* | (2006.01) | |
| *A61K 31/365* | (2006.01) | |
| *A61P 25/28* | (2006.01) | |
| *A61K 9/00* | (2006.01) | |
| *A61P 25/26* | (2006.01) | |
| *C07K 14/47* | (2006.01) | |

(52) U.S. Cl.
CPC .......... *A61K 31/366* (2013.01); *A61K 9/0019* (2013.01); *A61K 31/365* (2013.01); *A61P 25/26* (2018.01); *A61P 25/28* (2018.01); *C07K 14/4713* (2013.01)

(58) Field of Classification Search
CPC .. A61K 31/366; A61K 9/0019; A61K 31/365; A61P 25/26; A61P 25/14; A61P 25/24; A61P 25/28; C07K 14/4713
See application file for complete search history.

(56) References Cited

U.S. PATENT DOCUMENTS

| | | |
|---|---|---|
| 2008/0058396 A1 | 3/2008 | Alkon |
| 2018/0311209 A1 | 11/2018 | Alkon |

FOREIGN PATENT DOCUMENTS

| | | |
|---|---|---|
| WO | 2007/016202 A1 | 2/2007 |
| WO | 2014/145316 A1 | 9/2014 |
| WO | 2015/058191 A1 | 4/2015 |
| WO | 2015/148975 A1 | 10/2015 |

OTHER PUBLICATIONS

Ariza et al., J Biol Chem, vol. 286, No. 1, pp. 24-34, Jan. 7, 2011 (Year: 2011).*
Schrott et al., J Mol. Neurosci, 48:234-244, 2012 (Year: 2012).*
Wender et al., Organic Letters, vol. 8, No. 23: 5299-5302 (2006) (Year: 2006).*
Jayson et al., British Journal of Cancer, 72:461-468, (1995) (Year: 1995).*
Denvir et al. "Severe Alzheimer's Patient Responds to Bryostatin Treatment", Journal of Alzheimer's Disease, retrieved from the Internet, XP055328285 (Mar. 30, 2015).
Etcheberrigaray R. et al., "Therapeutic Effects of PKC Activators in Alzheimer's Disease Transgenic Mice", Proceedings of the National Academy of Science, National Academy of Science 101(30):11141-11146 (Jul. 2004).
Sun M-K et al., "Dual Effects of Bryostatin-1 on Spatial Memory and Depression", European Journal of Pharmacology 512(1):43-51 (Apr. 4, 2005).
ClinicalTrials.gov Identifier: NCT00606164, published Feb. 1, 2008.
International Search Report and Written Opinion dated Feb. 15, 2017 received in International Application No. PCT/US2016/056201.
Hongpaisan J. et al., "$PKC_\epsilon$ Activation Prevents Synaptic Loss, Aβ Elevation, and Cognitive Deficits in Alzheimer's Disease Transgenic Mice", The Journal of Neuroscience 31(2):630-643 (Jan. 12, 2011).
Patanella A.K. et al., "Correlations Between Peripheral Blood Mononuclear Cell Production of BDNF, TNF-alpha, IL-6, IL-10 and Cognitive Performances in Multiple Sclerosis Patients", Journal of Neuroscience Research 88:1106-1112 (2010).
Xiao J., "Neuroprotection on Mutliple Sclerosis: A BDNF Perspective", Journal of Neurology & Neurophysiology 3(3):e108 (2012).
Ziemssen T. et al., "Glatiramer Acetate-Specific T-Helper 1- and 2-Type Cell Lines Produce BDNF: Implications for Multiple Sclerosis Therapy", Brain 125:2381-2391 (2002).
Kornberg et al., PNAS, 115(9):2186-2191, (Feb. 27, 2018).

\* cited by examiner

*Primary Examiner* — Kimberly Ballard
*Assistant Examiner* — Stacey N MacFarlane
(74) *Attorney, Agent, or Firm* — Scully, Scott, Murphy & Presser, P.C.

(57) ABSTRACT

Dosing regimens and methods are disclosed for upregulating protein kinase C (PKC) while reducing subsequent down-regulation, comprising administering a PKC activator once a week for three consecutive weeks followed by cessation of administration or dosing for three consecutive weeks. Also described are methods for improving or enhancing cognitive ability, preventing or treating cognitive impairment, preventing or treating a neurodegenerative disease or condition, and/or preventing or treating a disease or condition associated with neuronal or synaptic loss according to the disclosed regimens.

7 Claims, 6 Drawing Sheets

DOSING REGIMENS OF PKC ACTIVATORS

CROSS REFERENCE TO RELATED APPLICATIONS

The present application is a continuation of U.S. patent application Ser. No. 16/513,058 filed on Jul. 16, 2019, which is a continuation of U.S. patent application Ser. No. 15/766,642, filed Apr. 6, 2018, which is a 371 of International Application having Serial No. PCT/US2016/056201, filed Oct. 8, 2016, which claims priority to U.S. Provisional Application 62/238,952, filed Oct. 8, 2015, the entire contents of which are incorporated herein by reference.

8, 2015, the entire contents of which are incorporated herein by reference.

Alzheimer's disease (AD) is a neurodegenerative disorder generally characterized by the progressive decline of mental functioning. More specifically, AD is characterized clinically by the progressive loss of memory, cognition, reasoning, judgment, and emotional stability that gradually leads to profound mental deterioration and, ultimately, death. Although there are many hypotheses for the possible mechanisms of AD, one central theory is that the excessive formation and accumulation of toxic beta-amyloid (AD) peptides either directly or indirectly affects a variety of cellular events and leads to neuronal damage and cell death. Selkoe, *Neuron.* 1991; 6(4):487-98 1991; Selkoe, *J. Clin Invest.* 2002; 110(10): 1375-81. Dementia associated with AD is referred to as senile dementia of the Alzheimer's type (SDAT) in usage with Alzheimer's disease.

AD is a progressive disorder with a mean duration of around 8-15 years between onset of clinical symptoms and death. AD is believed to represent the seventh most common medical cause of death and affects about 5 million people in the United States. There are three general stages of Alzheimer's disease: mild (early) stage, moderate (middle) stage and severe (late) stage. Each stage is associated with a worsening of neurological abilities. In the early (mild) stage, the subject may function independently, but experiences mild changes in cognitive functioning, such as memory lapses of recent events. The moderate stage, which is typically the longest stage and can last for many years, can be characterized by increased cognitive decline, significantly impacting memory and thinking, and interfering with routine functioning. The severe (late) stage of AD is characterized by further decline of mental functioning, such as losing the ability to communicate, to respond to surroundings, and to control movement and physical abilities.

Protein kinase C (PKC) is one of the largest gene families of protein kinase. Several PKC isozymes are expressed in the brain, including PKCα, PKCβ1, PKCβII, PKCδ, PKCε, and PKCγ. PKC is primarily a cytosolic protein, but with stimulation it translocates to the membrane.

PKC activators have been associated with prevention and treatment of various diseases and conditions. For example, PKC has been shown to be involved in numerous biochemical processes relevant to AD, and PKC activators have demonstrated neuroprotective activity in animal models of AD. PKC activation has a crucial role in learning and memory enhancement, and PKC activators have been shown to increase memory and learning. Sun and Alkon, *Eur J Pharmacol.* 2005; 512:43-51; Alkon et al., *Proc Nat Acad Sci USA.* 2005; 102:16432-16437. PKC activation also has been shown to induce synaptogenesis in rat hippocampus, suggesting the potential of PKC-mediated antiapoptosis and synaptogenesis during conditions of neurodegeneration. Sun and Alkon, *Proc Nat Acad Sci USA.* 2008; 105(36): 13620-13625. In fact, synaptic loss appears to be a pathological finding in the brain that is closely correlated with the degree of dementia in AD patients.

Neurotrophins, particularly brain-derived neurotrophic factor (BDNF) and nerve growth factor (NGF), are key growth factors that initiate repair and regrowth of damaged neurons and synapses. Activation of some PKC isoforms, particularly PKCε and PKCα, protect against neurological injury, most likely by upregulating the production of neurotrophins such as BDNF. Weinreb et al., *FASEB Journal.* 2004; 18:1471-1473). The activation of PKCε also increases brain postsynaptic density anchoring protein (PSD-95) which is an important marker for synaptogenesis.

In addition, changes in dendritic spine density form the basis of learning- and memory-induced changes in synaptic structure that increase synaptic strength. Abnormalities in the number and morphology of dendritic spines have been observed in many cognitive disorders, such as attention deficit hyperactivity disorder, schizophrenia, autism, mental retardation, and fragile X syndrome. For example, the brains of schizophrenic patients and people suffering from cognitive-mood disorders show a reduced number of dendritic spines in the brain areas associated with these diseases. In mental retardation and autism, the shapes of the dendritic spines are longer and appear more immature. Similarly, the only microscopic brain anomaly found in fragile X syndrome, the most common inherited form of mental retardation and autism, is the presence of thin, elongated immature dendritic spines.

PKC activation, for example, has further been shown to protect against traumatic brain injury-induced learning and memory deficits, (see Zohar et al., *Neurobiology of Disease,* 2011, 41: 329-337), has demonstrated neuroprotective activity in animal models of stroke, (see Sun et al., *Eur. J. Pharmacol.,* 2005, 512: 43-51), and has shown neuroprotective activity in animal models of depression, (see Sun et al., *Eur. J. Pharmacol.,* 2005, 512: 43-51).

Although PKC activation can produce numerous beneficial biological effects, such as those discussed above, as well as other known treatments and effects, research has shown that upregulating PKC can be difficult to achieve without also having downregulation that follows the upregulation. Thus, methods of upregulating PKC while reducing subsequent downregulation are needed to enhance beneficial effects associated with PKC activation.

In one aspect, the present disclosure provides an administration regimen, dosing regimen or method for upregulating PKC in a subject and reducing subsequent downregulation, comprising administering a PKC activator to the subject once a week for three consecutive weeks, followed by cessation of administration or dosing for three consecutive weeks.

In another aspect, the present disclosure relates to a spaced or intermittent dosing regimen of a PKC activator for improving or enhancing cognitive ability, preventing or treating cognitive impairment, preventing or treating a neurodegenerative disease or condition, and/or preventing or treating a disease or condition associated with neuronal or synaptic loss.

In one embodiment, the disclosure is directed to a dosing regimen for improving or enhancing a cognitive ability of a subject by administering to the subject a therapeutically effective amount of a PKC activator once a week for three consecutive weeks, followed by cessation of dosing for three consecutive weeks.

In another embodiment, the present disclosure provides a method for improving or enhancing cognitive ability of a subject, preventing or treating cognitive impairment of a subject in need thereof, treating or preventing a neurodegenerative disorder in a subject in need thereof, and/or preventing or treating a disease or condition associated with neuronal or synaptic loss in a subject in need thereof. The method comprises administering to the subject a therapeutically effective amount of a PKC activator once a week for three consecutive weeks, followed by cessation of dosing for three consecutive weeks.

DESCRIPTION

Figure 1:
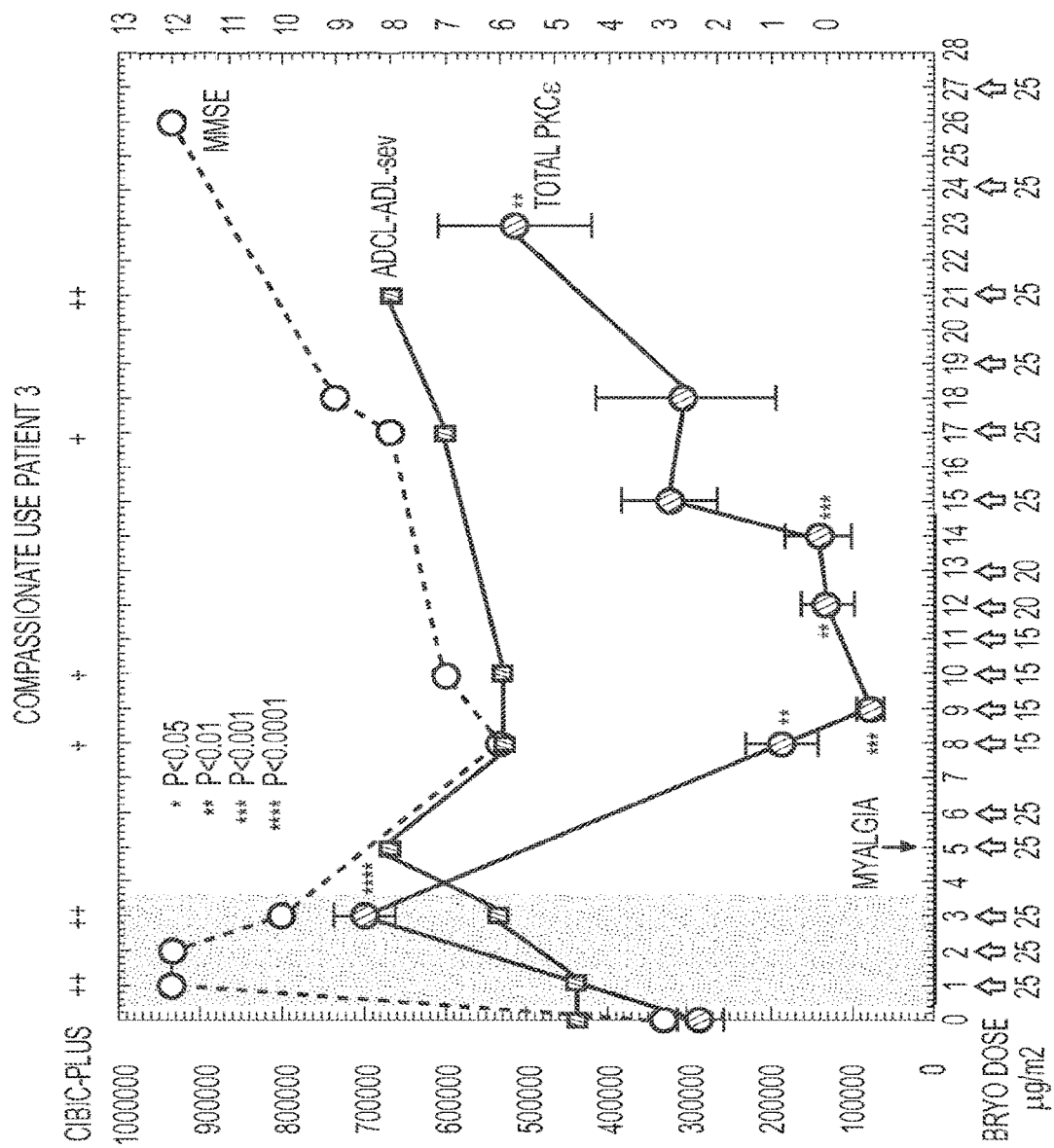
FIG. 1 illustrates, inter alia, the level of PKCε in the blood of a human subject receiving 25 μg/m² of bryostatin as a single weekly dose for three consecutive weeks followed by cessation of dosing for one week and then two additional weeks of dosing at 25 μg/m². The figure shows improved score on the Mini-Mental State Examination (MMSE) or Folstein test, an improvement of a primary efficacy outcome Activities of Daily Living—Severe Impairment Version (ADL-siv), and an increase in total PKC-ε levels in the patient during the first three consecutive weeks of dosing, followed by a decrease in MMSE, ADL-siv and total PKC-ε levels.

As used herein, the singular forms "a," "an," and "the" include plural reference.

As used herein, "protein kinase C activator" or "PKC activator" refers to a substance that increases the rate of the reaction catalyzed by PKC. PKC activators can be non-specific or specific activators. A specific activator activates one PKC isoform, e.g., PKC-ε (epsilon), to a greater detectable extent than another PKC isoform.

As used herein, the term "fatty acid" refers to a compound composed of a hydrocarbon chain and ending in a free acid, an acid salt, or an ester. When not specified, the term "fatty acid" is meant to encompass all three forms. Those skilled in the art understand that certain expressions are interchangeable. For example, "methyl ester of linolenic acid" is the same as "linolenic acid methyl ester," which is the same as "linolenic acid in the methyl ester form."

As used herein, the term "cyclopropanated" or "CP" refers to a compound wherein at least one carbon-carbon double bond in the molecule has been replaced with a cyclopropane group. The cyclopropyl group may be in cis or trans configuration. Unless otherwise indicated, it should be understood that the cyclopropyl group is in the cis configuration. Compounds with multiple carbon-carbon double bonds have many cyclopropanated forms. For example, a polyunsaturated compound in which only one double bond has been cyclopropanated would be said to be in "CP1 form." Similarly, "CP6 form" indicates that six double bonds are cyclopropanated.

For example, docosahexaenoic acid ("DHA") methyl ester has six carbon-carbon double bonds and thus can have one to six cyclopropane rings. Shown below are the CP1 and CP6 forms. With respect to compounds that are not completely cyclopropanated (e.g. DHA-CP1), the cyclopropane group(s) can occur at any of the carbon-carbon double bonds.

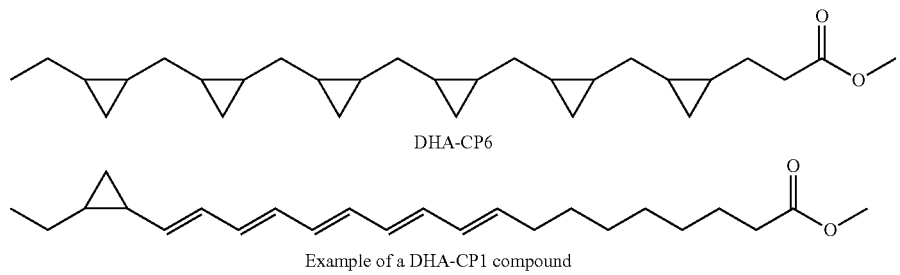

DHA-CP6

Example of a DHA-CP1 compound

As used herein, the word "cholesterol" refers to cholesterol and derivatives thereof. For example, "cholesterol" is understood to include the dihydrocholesterol species.

As used herein, the word "synaptogenesis" refers to a process involving the formation of synapses.

As used herein, the word "synaptic networks" refer to a multiplicity of neurons and synaptic connections between the individual neurons. Synaptic networks may include extensive branching with multiple interactions. Synaptic networks can be recognized, for example, by confocal visualization, electron microscopic visualization, and electrophysiologic recordings.

The phrases "cognitive ability" and "cognitive function" are used interchangeably in this application and refer to cerebral activities that encompass, for example, reasoning, memory, attention, and language. These phrases also encompass mental processes, such as awareness, perception, reasoning, and judgment. In one example, these phrases refer to brain-based skills necessary to carry out any task from the simplest to the most complex, such as learning, remembering, problem-solving, and paying attention.

The phrase "pharmaceutically acceptable" refers to molecular entities and compositions that are physiologically tolerable and do not typically produce untoward reactions when administered to a subject. For example, as used herein, the term "pharmaceutically acceptable" may refer to approved by a regulatory agency of the federal or a state government or listed in the U.S. Pharmacopeia or other generally recognized pharmacopeia for use in animals, and more particularly in humans. The term "pharmaceutically acceptable carrier" means a chemical composition with which the active ingredient may be combined and which, following the combination, can be used to administer the active ingredient to a subject and can refer to a diluent, adjuvant, excipient, or vehicle with which the compound is administered.

The term "therapeutically effective amount" refers to an amount of a therapeutic agent that results in a measurable or observable therapeutic response. A therapeutic response may be, for example, any response that a user (e.g., a clinician) will recognize as an effective response to the therapy, including improvement of symptoms and surrogate clinical markers. Thus, a therapeutic response will generally be an amelioration or inhibition of one or more symptoms of a disease or condition. A measurable therapeutic response also includes a finding that a symptom or disease is prevented or has a delayed onset, or is otherwise attenuated by the therapeutic agent.

The term "subject" refers to any mammal, such as a human in need of treatment with a PKC activator. For example, a subject may be a human in need of enhancement or improvement of cognitive ability, prevention or treatment of cognitive impairment, prevention or treatment of a neurodegenerative disorder, and/or prevention or treatment of a disease or condition associated with neuronal or synaptic loss. Illustrative of the term "subject" are humans, mice, rats, monkeys, and apes.

As used herein "Alzheimer's disease" encompasses Alzheimer's disease at any stage, for example mild or early stage, moderate or middle stage, and severe or late-stage.

The terms "approximately" and "about" mean to be nearly the same as a referenced number or value including an acceptable degree of error for the quantity measured given the nature or precision of the measurements. As used herein, the terms "approximately" and "about" should be generally understood to encompass±20% of a specified amount, frequency or value. Numerical quantities given herein are approximate unless stated otherwise, meaning that term "about" or "approximately" can be inferred when not expressly stated.

The terms "administer," "administration," or "administering" as used herein refer to (1) providing, giving, dosing and/or prescribing by either a health practitioner or his authorized agent or under his direction a composition according to the disclosure, and (2) putting into, taking or consuming by the patient or person himself or herself, a composition according to the disclosure. As used herein, "administration" of a composition includes any route of administration, including oral, intravenous, subcutaneous, intraperitoneal, and intramuscular.

The phrase "weekly dosing regimen" is used when the subject is administered a dose of a therapeutic agent (drug) every week for a predetermined number of consecutive weeks. For example, the subject receives a single dose of a therapeutic agent each week for three consecutive weeks.

The phrases "spaced dosing regimen" and "intermittent dosing regimen" are used interchangeably in the application and refer to an on/off dosing regimen of a defined periodicity.

The present disclosure relates to, inter alia, the unexpected finding that a spaced dosing regimen or intermittent dosing regimen as described herein for administering a PKC activator to a subject substantially upregulated PKC, thereby providing desired beneficial effects of PKC activation, while reducing the subsequent downregulation observed in previously-used dosing regimens of PKC activators.

The present disclosure provides an administration regimen, dosing regimen or method for upregulating PKC in a subject and reducing subsequent downregulation, comprising administering a PKC activator to the subject once a week for three consecutive weeks, followed by cessation of administration or dosing for three consecutive weeks.

In some embodiments, the administration may continue in alternating intervals of administering the PKC activator once a week for three consecutive weeks, followed by cessation of administration or dosing for three consecutive weeks, such as continuing those alternating intervals over a period of about 4 months, about 8 months, about 1 year, about 2 years, about 5 years, or otherwise for the duration of therapy with the PKC activator.

In at least one embodiment, the PKC activator is chosen from macrocyclic lactones, bryologs, diacylglcerols, isoprenoids, octylindolactam, gnidimacrin, ingenol, iripallidal, napthalenesulfonamides, diacylglycerol inhibitors, growth factors, polyunsaturated fatty acids, monounsaturated fatty acids, cyclopropanated polyunsaturated fatty acids, cyclopropanated monounsaturated fatty acids, fatty acids alcohols and derivatives, and fatty acid esters.

In at least one embodiment, the PKC activator is a macrocyclic lactone chosen from bryostatin and neristatin, such as neristatin-1. In a further embodiment, the PKC activator is bryostatin, such as bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, or bryostatin-18. In a further embodiment, the PKC activator is bryostatin-1.

The PKC activator may be administered according to the spaced dosing regimens or intermittent dosing regimens described herein in an amount that is the same or different from week to week. In some embodiments, the PKC activator, such as bryostatin (e.g., bryostatin-1) may be administered in an amount ranging from about 0.01 $\mu g/m^2$ to about 100 $\mu g/m^2$. In at least one embodiment, the amount is about 10 $\mu g/m^2$, about 15 $\mu g/m^2$, about 20 $\mu g/m^2$, about 25 $\mu g/m^2$, about 30 $\mu g/m^2$, about 35 $\mu g/m^2$, about 40 $\mu g/m^2$, about 45 $\mu g/m^2$, about 50 $\mu g/m^2$, about 55 $\mu g/m^2$, about 60 $\mu g/m^2$, about 65 $\mu g/m^2$, about 70 $\mu g/m^2$, about 75 $\mu g/m^2$, about 80 $\mu g/m^2$, about 85 $\mu g/m^2$, about 90 $\mu g/m^2$, about 95 $\mu g/m^2$, or about 100 $\mu g/m^2$. In some embodiments, the amount may range from about 10-40 $\mu g/m^2$, for example, about 15 $\mu g/m^2$, about 20 $\mu g/m^2$, about 25 $\mu g/m^2$, about 30 $\mu g/m^2$, about 35 $\mu g/m^2$, or about 40 $\mu g/m^2$.

In some embodiments, the PKC activator is administered as a dose in the range of about 0.01 to 100 µg/m²/week. In at least one embodiment, the dose administered each week can range from about 0.01 to about 25 µg/m²/week; about 1 to about 20 µg/m²/week, about 5 to about 20 µg/m²/week, or about 10 to about 20 µg/m²/week. For certain embodiments, the dose may be about 5 µg/m²/week, about 10 µg/m²/week, about 15 µg/m²/week, or about 20 µg/m²/week.

In a further aspect, the role of such intermittent dosing of a PKC activator on restoring or upregulating BDNF, increasing the postsynaptic density of the anchoring protein PSD-95, and lowering or preventing the downregulation of PCK-ε, which is the neurological target of the PKC activator bryostatin is disclosed.

BDNF is a peptide that is implicated to induce synaptogenesis and improve cognitive function. Although evidence for BDNF polymorphisms in AD is still inconclusive, synaptic loss is the single most important correlate of AD. Lower BDNF levels are associated in AD cases with apathy, a noncognitive symptom common to many forms of dementia (Alvarez et al., Apathy and APOE4 are associated with reduced BDNF levels in Alzheimer's disease, *J. Alzheimers Dis.*, 42:1347-1355, 2014). While BDNF expression is regulated by at least nine promoters (Aid et al., Mouse and rat BDNF gene structure and expression revisited, *J. Neurosci. Res.*; 85:525-535, 2007; Pruunsild et al., Dissecting the human BDNF locus: bidirectional transcription, complex splicing, and multiple promoters, *Genomics*, 90:397-406, 2007), promoter IV (PIV) is most responsive to neuronal activity (Tao et al., Ca2 influx regulates BDNF transcription by a CREB family transcription factor-dependent mechanism, *Neuron*, 20:709-726, 1998). PKCε, which is decreased in AD (Hongpaisan et al., PKC epsilon activation prevents synaptic loss, Abeta elevation, and cognitive deficits in Alzheimer's disease transgenic mice, *J. Neurosci.*, 31:630-643, 2011; Khan et al., PKC-epsilon deficits in Alzheimer's disease brains and skin fibroblasts, *J. Alzheimers Dis.*, 43:491-509, 2015), also regulates BDNF expression (Lim and Alkon, 2012; Corbett et al., 2013; Hongpaisan et al., PKC activation during training restores mushroom spine synapses and memory in the aged rat, *Neurobiol. Dis.*, 55:44-62, 2013; Neumann et al., Increased BDNF protein expression after ischemic or PKC epsilon preconditioning promotes electrophysiologic changes that lead to neuroprotection, *J. Cereb. Blood Flow Metab.*, 35:121-130, 2015).

FIG. 1 illustrates early results of a compassionate use (CU) study involving human advanced AD patients. The study evaluated the effect of bryostatin-1 on the patients' cognitive function. The administration comprised three consecutive weeks of dosing followed by cessation for one week and then two additional weeks of dosing. Standard psychometric tests were used to measure cognitive functions and behaviors. The study also evaluated the relationship between the level of bryostatin's target, PKC epsilon, in the blood and the cognitive measurements.

The shaded area of FIG. 1 shows improved cognitive function in an advanced AD patient that was administered a weekly 25 µg/m² dose of the PKC activator bryostatin for three consecutive weeks. For example, patients receiving bryostatin at a weekly dose of 25 µg/m² showed improvements in the Mini-Mental State Examination (MMSE) score as well as improvements in their primary efficacy outcome Activities of Daily Living—Severe Impairment Version (ADL-siv). Observed improvements included restored speech and word recognition, restored swallowing, lowered or prevented hallucinations, and improved complex motor functions. Administering bryostatin at a weekly dose of 25 µg/m² for three consecutive weeks also increased total PKC-ε levels. This dose of bryostatin also improved the behavior of the AD subjects. For example, the observed behavioral improvements included restoration of speech and word recognition, restoration of swallowing, disappearance of hallucinations, return of complex motor activity, including swimming, billiards, conversational interactions, and orientation in time and space.

However, as shown in FIG. 1, a decline in the observed benefits (cognitive function and behavior), was seen in the weeks that followed at varying dose level and frequencies of dosing, as indicated by the psychometric scores. In particular, despite additional bryostatin dosing in weeks 5, 6, and 8-13, as shown in FIG. 1, the administration failed to maintain the observed cognitive benefits seen in the patients after the first three consecutive weeks of bryostatin administration. The decline closely tracked the decline in PCK-ε levels, as illustrated in FIG. 1. The observed decline was due to a well-known phenomenon that follows PKC activation called "downregulation". Sustained clinical improvements in these patients with advanced AD were mitigated by the downregulation of the bryostatin target, PKC-ε. From these preliminary observations the inventors hypothesized that an intermittent dosing regimen of bryostatin was more suitable for maintaining cognitive benefits in AD patients.

The spaced dosing regimen or intermittent dosing regimen according to the present disclosure, however, substantially upregulates PKC, thereby providing cognitive and treatment benefits, while reducing the subsequent downregulation observed in previously-used dosing regimens of PKC activators.

Specifically, in at least one embodiment according to the present disclosure, a dosing regimen for improving or enhancing a cognitive ability of a subject comprises administering to the subject a therapeutically effective amount of a PKC activator once a week for three consecutive weeks, followed by cessation of dosing for three consecutive weeks.

In another embodiment of the present disclosure, a method for improving or enhancing cognitive ability of a subject, preventing or treating cognitive impairment of a subject in need thereof, treating or preventing a neurodegenerative disorder in a subject in need thereof, and/or preventing or treating a disease or condition associated with neuronal or synaptic loss in a subject in need thereof, comprises administering to the subject a therapeutically effective amount of a PKC activator once a week for three consecutive weeks, followed by cessation of dosing for three consecutive weeks.

In at least one embodiment, the subject is in need of treatment for a neurodegenerative disorder, such as Alzheimer's disease, chronic traumatic encephalopathy (CTE), Parkinson's disease, traumatic brain injury, Fragile X, Niemann-Pick C, frontotemporal dementia, vascular dementia, depression, bipolar disorder, schizophrenia, Post-Traumatic Stress Disorder, stroke, mental retardation, or brain injury. In at least one embodiment, the neurodegenerative disorder is Alzheimer's disease.

In some embodiments, the administration may continue in alternating intervals of administering a therapeutically effective amount of a PKC activator once a week for three consecutive weeks, followed by cessation of dosing for three consecutive weeks, such as continuing in those alternating intervals over a period of about 4 months, about 8 months, about 1 year, about 2 years, about 5 years, or otherwise for the duration of therapy with the PKC activator.

In at least one embodiment, the PKC activator is chosen from macrocyclic lactones, bryologs, diacylglcerols, isoprenoids, octylindolactam, gnidimacrin, ingenol, iripallidal, napthalenesulfonamides, diacylglycerol inhibitors, growth factors, polyunsaturated fatty acids, monounsaturated fatty acids, cyclopropanated polyunsaturated fatty acids, cyclopropanated monounsaturated fatty acids, fatty acids alcohols and derivatives, and fatty acid esters. In at least one embodiment, the PKC activator is a macrocyclic lactone chosen from bryostatin and neristatin, such as neristatin-1. In a further embodiment, the PKC activator is bryostatin, such as bryostatin-1, bryostatin-2, bryostatin-3, bryostatin-4, bryostatin-5, bryostatin-6, bryostatin-7, bryostatin-8, bryostatin-9, bryostatin-10, bryostatin-11, bryostatin-12, bryostatin-13, bryostatin-14, bryostatin-15, bryostatin-16, bryostatin-17, or bryostatin-18. In a further embodiment, the PKC activator is bryostatin-1. In at least one embodiment, the therapeutically effective amount of the PKC activator, such as bryostatin-1, is about 25 μg/m².

In at least one embodiment, the dosing regimens of the present disclosure are used to treat or prevent Alzheimer's Disease. In at least one embodiment, the subject is a human with moderate-to-severe or severe (i.e., late-stage or advanced) Alzheimer's disease.

The therapeutically effective amount administered according to the spaced dosing regimens or intermittent dosing regimens described herein may be the same or different from week to week. The therapeutically effective amount of the PKC activator, such as bryostatin (e.g., bryostatin-1) may range, for example, from about 0.01 μg/m² to about 100 μg/m². In at least one embodiment, the therapeutically effective amount is about 10 μg/m², about 15 μg/m², about 20 μg/m², about 25 μg/m², about 30 μg/m², about 35 μg/m², about 40 μg/m² about 45 μg/m², about 50 μg/m², about 55 μg/m², about 60 μg/m², about 65 μg/m², about 70 μg/m², about 75 μg/m², about 80 μg/m², about 85 μg/m², about 90 μg/m², about 95 μg/m², or about 100 μg/m². For certain embodiments, the therapeutically effective amount may range from about 10-40 μg/m², for example, about 15 μg/m², about 20 μg/m², about 25 μg/m², about 30 μg/m², about 35 μg/m², or about 40 μg/m².

Appropriate doses of the PKC activator may be, for example, about 0.01 to 100 μg/m²/week. In at least one embodiment, the dose administered each week can range from about 0.01 to about 25 μg/m²/week; about 1 to about 20 μg/m²/week, about 5 to about 20 μg/m²/week, or about 10 to about 20 μg/m²/week. For certain embodiments, the appropriate dose may be about 5 μg/m²/week, about 10 μg/m²/week, about 15 μg/m²/week, or about 20 μg/m²/week.

In at least one embodiment, the subject is dosed for three consecutive weeks using a pharmaceutical composition of the invention followed by cessation of dosing for 3 weeks (i.e., 3on/3off). This regimen may be continued, for example, in alternating 3on/3off intervals.

The dosing regimens and methods according to the present disclosure are not limited to any specific PKC activator. For example, the PKC activator may be a macrocyclic lactone. Macrocyclic lactones (also known as macrolides) generally comprise 14-, 15-, or 16-membered lactone rings. Macrolides belong to the polyketide class of natural products. Macrocyclic lactones and derivatives thereof are described, for example, in U.S. Pat. Nos. 6,187,568; 6,043,270; 5,393,897; 5,072,004; 5,196,447; 4,833,257; and 4,611,066; and 4,560,774; each incorporated by reference herein in its entirety. Those patents describe various compounds and various uses for macrocyclic lactones including their use as an anti-inflammatory or anti-tumor agents. See also Szallasi et al. *J. Biol. Chem.* (1994), vol. 269, pp. 2118-2124; Zhang et al., *Cancer Res.* (1996), vol. 56, pp. 802-808; Hennings et al. *Carcinogenesis* (1987), vol. 8, pp. 1343-1346; Varterasian et al. *Clin. Cancer Res.* (2000), vol. 6, pp. 825-828; Mutter et al. *Bioorganic & Med. Chem.* (2000), vol. 8, pp. 1841-1860; each incorporated by reference herein in its entirety.

In at least one embodiment of the present disclosure, the macrocyclic lactone is a bryostatin. Bryostatins include, for example, Bryostatin-1, Bryostatin-2, Bryostatin-3, Bryostatin-4, Bryostatin-5, Bryostatin-6, Bryostatin-7, Bryostatin-8, Bryostatin-9, Bryostatin-10, Bryostatin-11, Bryostatin-12, Bryostatin-13, Bryostatin-14, Bryostatin-15, Bryostatin-16, Bryostatin-17, and Bryostatin-18.

In at least one embodiment, the bryostatin is Bryostatin-1 (shown below).

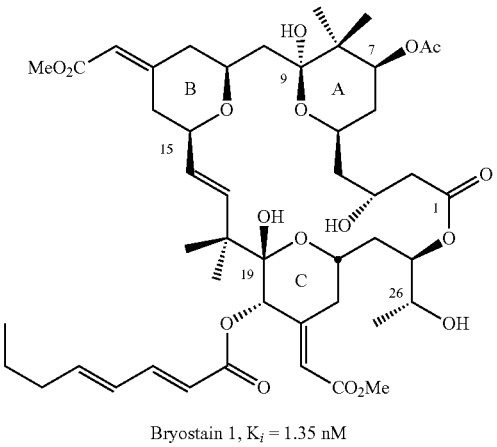

Bryostain 1, $K_i$ = 1.35 nM

In another embodiment, the bryostatin is Bryostatin-2 (shown below; R=COC$_7$H$_{11}$, R'=H).

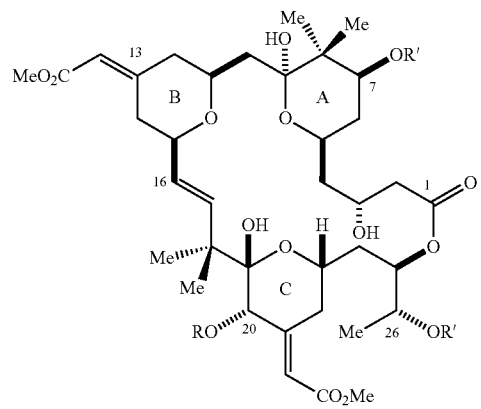

In at least one embodiment of the present disclosure, the macrocyclic lactone is a neristatin. In at least one embodiment, the neristatin is chosen from neristatin-1. In another embodiment, the macrocyclic lactone is chosen from macrocylic derivatives of cyclopropanated PUFAs such as, 24-octaheptacyclononacosan-25-one (cyclic DHA-CP6) (shown below).

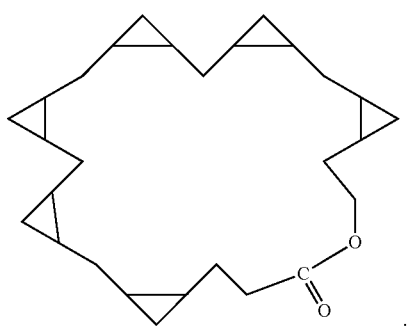 [SMILES: O=C1CCC2CC2CC2CC2CC2CC2CC2CC2CC2CC2CC2CC2CCO1]

In another embodiment, the macrocyclic lactone is a bryolog. Bryologs (analogs of bryostatin) are another class of PKC activators that are suitable for use in the present disclosure. Bryologs can be chemically synthesized or produced by certain bacteria. Different bryologs exist that modify, for example, the rings A, B, and C (see Bryostatin-1, figure shown above) as well as the various substituents. As a general overview, bryologs are considered less specific and less potent than bryostatin but are easier to prepare. It was found that the C-ring is important for binding to PKC while the A-ring is important for non-tumorigenesis. Further, the hydrophobic tail appears to be important for membrane binding.

Table 1 summarizes structural characteristics of several bryologs and demonstrates variability in their affinity for PKC (ranging from 0.25 nM to 10 μM). Structurally, they are all similar. While Bryostatin-1 has two pyran rings and one 6-membered cyclic acetal, in most bryologs one of the pyrans of Bryostatin-1 is replaced with a second 6-membered acetal ring. This modification may reduce the stability of bryologs, relative to Bryostatin-1, for example, in both strong acid or base, but has little significance at physiological pH. Bryologs also have a lower molecular weight (ranging from about 600 g/mol to 755 g/mol), as compared to Bryostatin-1 (988), a property which may facilitate transport across the blood-brain barrier.

TABLE 1

| Bryologs | | | |
|---|---|---|---|
| Name | PKC Affin (nM) | MW | Description |
| Bryostatin-1 | 1.35 | 988 | 2 pyran + 1 cyclic acetal + macrocycle |
| Analog 1 | 0.25 | 737 | 1 pyran + 2 cyclic acetal + macrocycle |
| Analog 2 | 6.50 | 723 | 1 pyran + 2 cyclic acetal + macrocycle |
| Analog 7a | — | 642 | 1 pyran + 2 cyclic acetals + macrocycle |
| Analog 7b | 297 | 711 | 1 pyran + 2 cyclic acetals + macrocycle |
| Analog 7c | 3.4 | 726 | 1 pyran + 2 cyclic acetals + macrocycle |
| Analog 7d | 10000 | 745 | 1 pyran + 2 cyclic acetals + macrocycle, acetylated |
| Analog 8 | 8.3 | 754 | 2 cyclic acetals + macrocycle |
| Analog 9 | 10000 | 599 | 2 cyclic acetals |

Analog 1 exhibits the highest affinity for PKC. Wender et al., *Curr. Drug Discov. Technol.* (2004), vol. 1, pp. 1-11; Wender et al. *Proc. Nat. Acad. Sci.* (1998), vol. 95, pp. 6624-6629; Wender et al., *J. Am. Chem. Soc.* (2002), vol. 124, pp. 13648-13649, each incorporated by reference herein in their entireties. Only Analog 1 exhibits a higher affinity for PKC than Bryostatin-1. Analog 2, which lacks the A ring of Bryostatin-1, is the simplest analog that maintains high affinity for PKC. In addition to the active bryologs, Analog 7d, which is acetylated at position 26, has virtually no affinity for PKC.

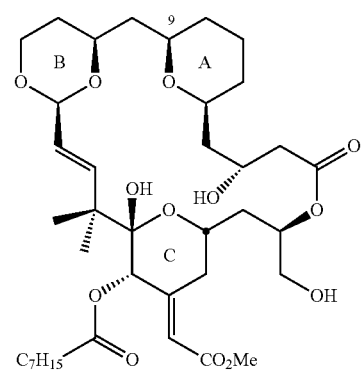

Analog 1: $K_i = 0.25$ nM

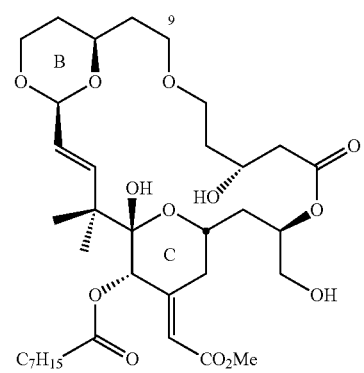

Analog 2: $K_i = 8.0$ nM

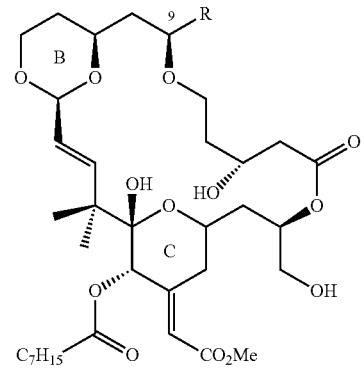

3 R = t-Bu
4 R = Ph
5 R = $(CH_2)_3$p-Br-Ph

B-ring bryologs may also be used in the present disclosure. These synthetic bryologs have affinities in the low nanomolar range. Wender et al., *Org Lett.* (2006), vol. 8, pp. 5299-5302, incorporated by reference herein in its entirety.

B-ring bryologs have the advantage of being completely synthetic, and do not require purification from a natural source.

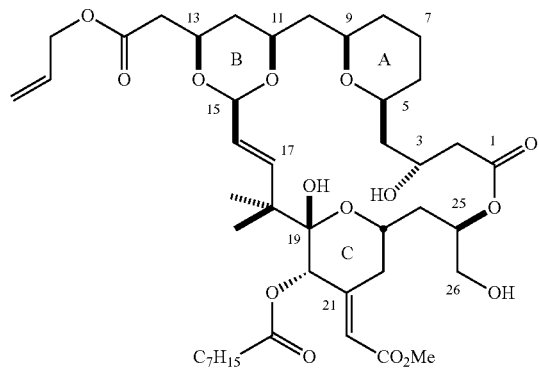

3: PKC $K_i$ = 1.2 ± 0.6 nM

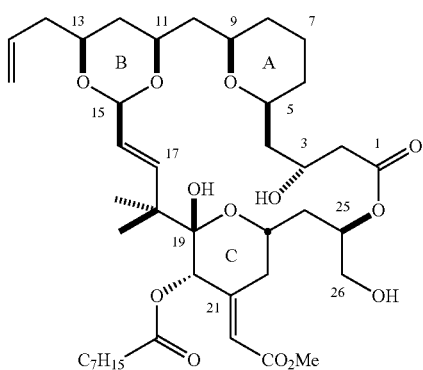

4: PKC $K_i$ = 0.67 ± 0.5 nM

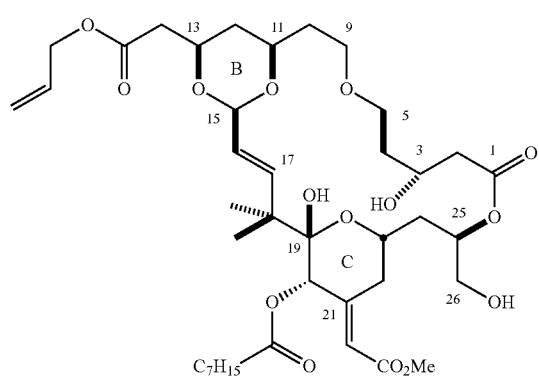

5: PKC $K_i$ = 3.0 ± 0.5 nM

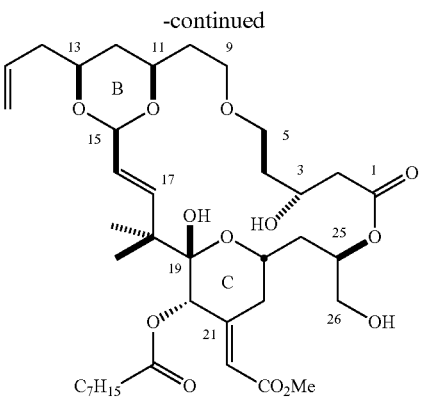

6: PKC $K_i$ = 2.6 ± 0.5 nM

A third class of suitable bryostatin analogs are the A-ring bryologs. These bryologs have slightly lower affinity for PKC than Bryostatin-1 (6.5 nM, 2.3 nM, and 1.9 nM for bryologs 3, 4, and 5, respectively) and a lower molecular weight. A-ring substituents are important for non-tumorigenesis.

Bryostatin analogs are described, for example, in U.S. Pat. Nos. 6,624,189 and 7,256,286. Methods using macrocyclic lactones to improve cognitive ability are also described in U.S. Pat. No. 6,825,229 B2.

Another class of PKC activators is derivatives of diacylglycerols that bind to and activate PKC. See, e.g., Niedel et al., *Proc. Nat. Acad. Sci.* (1983), vol. 80, pp. 36-40; Mori et al., *J. Biochem.* (1982), vol. 91, pp. 427-431; Kaibuchi et al., *J. Biol. Chem.* (1983), vol. 258, pp. 6701-6704. Activation of PKC by diacylglycerols is transient, because they are rapidly metabolized by diacylglycerol kinase and lipase. Bishop et al. *J. Biol. Chem.* (1986), vol. 261, pp. 6993-7000; Chuang et al. *Am. J. Physiol.* (1993), vol. 265, pp. C927-C933; incorporated by reference herein in their entireties. The fatty acid substitution on the diacylglycerols derivatives may determine the strength of activation. Diacylglycerols having an unsaturated fatty acid may be most active. The stereoisomeric configuration is important; fatty acids with a 1,2-sn configuration may be active while 2,3-sn-diacylglycerols and 1,3-diacylglycerols may not bind to PKC. Cis-unsaturated fatty acids may be synergistic with diacylglycerols. In at least one embodiment, the term "PKC activator" expressly excludes DAG or DAG derivatives.

Another class of PKC activators is isoprenoids. Farnesyl thiotriazole, for example, is a synthetic isoprenoid that activates PKC with a $K_d$ of 2.5 µM. Farnesyl thiotriazole, for example, is equipotent with dioleoylglycerol, but does not possess hydrolyzable esters of fatty acids. Gilbert et al., *Biochemistry* (1995), vol. 34, pp. 3916-3920; incorporated by reference herein in its entirety. Farnesyl thiotriazole and related compounds represent a stable, persistent PKC activator. Because of its low molecular weight (305.5 g/mol) and absence of charged groups, farnesyl thiotriazole may be expected to readily cross the blood-brain barrier.

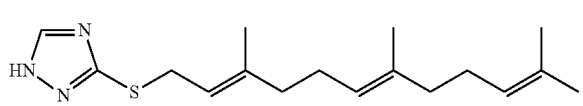 [SMILES: CC(C)=CCC/C(C)=C/CC/C(C)=C/CSc1nc[nH]n1]

Yet another class of activators includes octylindolactam V, gnidimacrin, and ingenol. Octylindolactam V is a nonphorbol protein kinase C activator related to teleocidin. The advantages of octylindolactam V (specifically the (−)-enantiomer) may include greater metabolic stability, high potency (EC$_{50}$=29 nM) and low molecular weight that facilitates transport across the blood brain barrier. Fujiki et al. *Adv. Cancer Res.* (1987), vol. 49 pp. 223-264; Collins et al. *Biochem. Biophys. Res. Commun.* (1982), vol. 104, pp. 1159-4166, each incorporated by reference herein in its entirety.

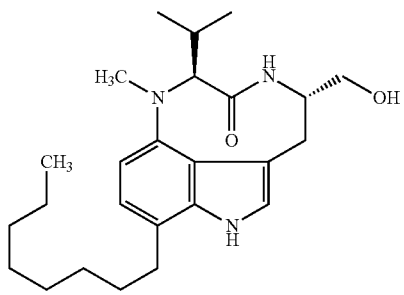 [SMILES: CCCCCCCCc1ccc2c3c(c[nH]c13)C[C@@H](CO)NC(=O)[C@H](C(C)C)N2C]

Gnidimacrin is a daphnane-type diterpene that displays potent antitumor activity at concentrations of 0.1 nM-1 nM against murine leukemias and solid tumors. It may act as a PKC activator at a concentration of 0.3 nM in K562 cells, and regulate cell cycle progression at the G1/S phase through the suppression of Cdc25A and subsequent inhibition of cyclin dependent kinase 2 (Cdk2) (100% inhibition achieved at 5 ng/ml). Gnidimacrin is a heterocyclic natural product similar to Bryostatin-1, but somewhat smaller (MW=774.9 g/mol).

Iripallidal is a bicyclic triterpenoid isolated from *Iris pallida*. Iripallidal displays anti-proliferative activity in a NC 60 cell line screen with GI$_{50}$ (concentration required to inhibit growth by 50%) values from micromolar to nanomolar range. It binds to PKCα with high affinity (K$_i$=75.6 nM). It may induce phosphorylation of Erk1/2 in a Ras-GRP3-dependent manner. Its molecular weight is 486.7 g/mol. Iripallidal is about half the size of Bryostatin-1 and lacks charged groups.

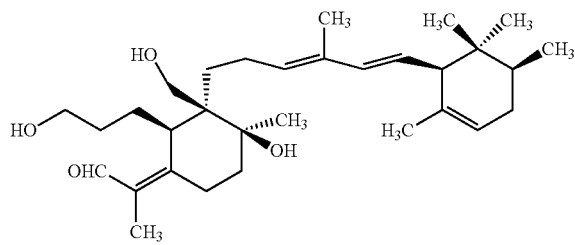

Ingenol is aditerpenoid related to phorbol but less toxic. It is derived from the milkweed plant *Euphorbia peplus*. Ingenol 3,20-dibenzoate, for example, competes with [3H] phorbol dibutyrate for binding to PKC (K$_i$=240 nM). Winkler et al., *J. Org. Chem.* (1995), vol. 60, pp. 1381-1390, incorporated by reference herein. Ingenol-3-angelate exhibits antitumor activity against squamous cell carcinoma and melanoma when used topically. Ogbourne et al. *Anticancer Drugs* (2007), vol. 18, pp. 357-362, incorporated by reference herein.

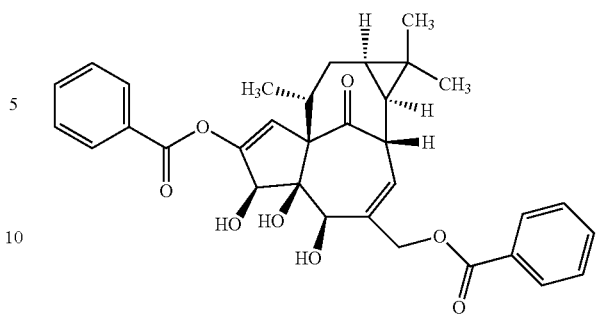

Another class of PKC activators is napthalenesulfonamides, including N-(n-heptyl)-5-chloro-1-naphthalenesulfonamide (SC-10) and N-(6-phenylhexyl)-5-chloro-1-naphthalenesulfonamide. SC-10 may activate PKC in a calcium-dependent manner, using a mechanism similar to that of phosphatidylserine. Ito et al., *Biochemistry* (1986), vol. 25, pp. 4179-4184, incorporated by reference herein. Naphthalenesulfonamides act by a different mechanism than bryostatin and may show a synergistic effect with bryostatin or member of another class of PKC activators. Structurally, naphthalenesulfonamides are similar to the calmodulin (CaM) antagonist W-7, but are reported to have no effect on CaM kinase.

Yet another class of PKC activators is diacylglycerol kinase inhibitors, which indirectly activate PKC. Examples of diacylglycerol kinase inhibitors include, but are not limited to, 6-(2-(4-[(4-fluorophenyl)phenylmethylene]-1-piperidinyl)ethyl)-7-methyl-5H-thiazolo[3,2-a]pyrimidin-5-one (R59022) and [3-[2-[4-(bis-(4-fluorophenyl)methylene] piperidin-1-yl)ethyl]-2,3-dihydro-2-thioxo-4(1H)-quinazolinone (R59949).

Still another class of PKC activators is growth factors, such as fibroblast growth factor 18 (FGF-18) and insulin growth factor, which function through the PKC pathway. FGF-18 expression is up-regulated in learning, and receptors for insulin growth factor have been implicated in learning. Activation of the PKC signaling pathway by these or other growth factors offers an additional potential means of activating PKC.

Another class of PKC activators is hormones and growth factor activators, including 4-methyl catechol derivatives like 4-methylcatechol acetic acid (MCBA) that stimulate the synthesis and/or activation of growth factors such as NGF and BDNF, which also activate PKC as well as convergent pathways responsible for synaptogenesis and/or neuritic branching.

Further example PKC activators include polyunsaturated fatty acids ("PUFAs"). These compounds are essential components of the nervous system and have numerous health benefits. In general, PUFAs increase membrane fluidity, rapidly oxidize to highly bioactive products, produce a variety of inflammatory and hormonal effects, and are rapidly degraded and metabolized. The inflammatory effects and rapid metabolism is likely the result of their active carbon-carbon double bonds. These compounds may be potent activators of PKC, most likely by binding the PS site.

In at least one embodiment, the PUFA is chosen from linoleic acid (shown below).

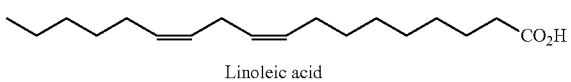

Linoleic acid

Another class of PKC activators is PUFA and MUFA derivatives, and cyclopropanated derivatives in particular. Certain cyclopropanated PUFAs, such as DCPLA (i.e., linoleic acid with cyclopropane at both double bonds), may be able to selectively activate PKC-ε. See *Journal of Biological Chemistry*, 2009, 284(50): 34514-34521; see also U.S. Patent Application Publication No. 2010/0022645 A1. Like their parent molecules, PUFA derivatives are thought to activate PKC by binding to the PS site.

Cyclopropanated fatty acids exhibit low toxicity and are readily imported into the brain where they exhibit a long half-life ($t_{1/2}$). Conversion of the double bonds into cyclopropane rings prevents oxidation and metabolism to inflammatory byproducts and creates a more rigid U-shaped 3D structure that may result in greater PKC activation. Moreover, this U-shape may result in greater isoform specificity. For example, cyclopropanated fatty acids may exhibit potent and selective activation of PKC-ε.

The Simmons-Smith cyclopropanation reaction is an efficient way of converting double bonds to cyclopropane groups. This reaction, acting through a carbenoid intermediate, preserves the cis-stereochemistry of the parent molecule. Thus, the PKC-activating properties are increased while metabolism into other molecules like bioreactive eicosanoids, thromboxanes, or prostaglandins is prevented.

One class of PKC-activating fatty acids is Omega-3 PUFA derivatives. In at least one embodiment, the Omega-3 PUFA derivatives are chosen from cyclopropanated docosahexaenoic acid, cyclopropanated eicosapentaenoic acid, cyclopropanated rumelenic acid, cyclopropanated parinaric acid, and cyclopropanated linolenic acid (CP3 form shown below).

Another class of PKC-activating fatty acids is Omega-6 PUFA derivatives. In at least one embodiment, the Omega-6 PUFA derivatives are chosen from cyclopropanated linoleic acid ("DCPLA," CP2 form shown below),

cyclopropanated arachidonic acid, cyclopropanated eicosadienoic acid, cyclopropanated dihomo-gamma-linolenic acid, cyclopropanated docosadienoic acid, cyclopropanated adrenic acid, cyclopropanated calendic acid, cyclopropanated docosapentaenoic acid, cyclopropanated jacaric acid, cyclopropanated pinolenic acid, cyclopropanated podocarpic acid, cyclopropanated tetracosatetraenoic acid, and cyclopropanated tetracosapentaenoic acid.

Vernolic acid is a naturally occurring compound. However, it is an epoxyl derivative of linoleic acid and therefore, as used herein, is considered an Omega-6 PUFA derivative. In addition to vernolic acid, cyclopropanated vernolic acid (shown below) is an Omega-6 PUFA derivative.

Another class of PKC-activating fatty acids is Omega-9 PUFA derivatives. In at least one embodiment, the Omega-9 PUFA derivatives are chosen from cyclopropanated eicosenoic acid, cyclopropanated mead acid, cyclopropanated erucic acid, and cyclopropanated nervonic acid.

Yet another class of PKC-activating fatty acids is monounsaturated fatty acid ("MUFA") derivatives. In at least one embodiment, the MUFA derivatives are chosen from cyclopropanated oleic acid (shown below),

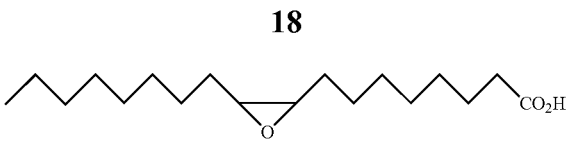

and cyclopropanated elaidic acid (shown below).

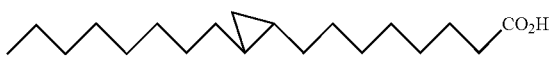 [SMILES: CCCCCCCCC1CC1CCCCCCCC(=O)O]

PKC-activating MUFA derivatives include epoxylated compounds such as trans-9,10-epoxystearic acid (shown below).

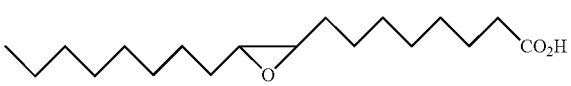 [SMILES: CCCCCCCCC1OC1CCCCCCCC(=O)O]

Another class of PKC-activating fatty acids is Omega-5 and Omega-7 PUFA derivatives. In at least one embodiment, the Omega-5 and Omega-7 PUFA derivatives are chosen from cyclopropanated rumenic acid, cyclopropanated alpha-elosteric acid, cyclopropanated catalpic acid, and cyclopropanated punicic acid.

Another class of PKC activators is fatty acid alcohols and derivatives thereof, such as cyclopropanated PUFA and MUFA fatty alcohols. It is thought that these alcohols activate PKC by binding to the PS site. These alcohols can be derived from different classes of fatty acids.

In at least one embodiment, the PKC-activating fatty alcohols are derived from Omega-3 PUFAs, Omega-6 PUFAs, Omega-9 PUFAs, and MUFAs, especially the fatty acids noted above. In at least one embodiment, the fatty alcohol is chosen from cyclopropanated linolenyl alcohol (CP3 form shown below),

cyclopropanated linoleyl alcohol (CP2 form shown below),

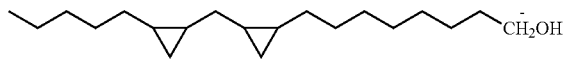 [SMILES: CCCCCC1CC1CC1CC1CCCCCCCCO]

cyclopropanated elaidic alcohol (shown below),

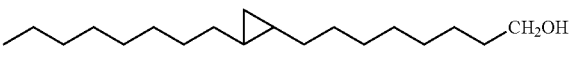 [SMILES: CCCCCCCCC1CC1CCCCCCCCO]

cyclopropanated DCPLA alcohol, and cyclopropanated oleyl alcohol.

Another class of PKC activators is fatty acid esters and derivatives thereof, such as cyclopropanated PUFA and MUFA fatty esters. In at least one embodiment, the cyclopropanated fatty esters are derived from Omega-3 PUFAs, Omega-6 PUFAs, Omega-9 PUFAs, MUFAs, Omega-5 PUFAs, and Omega-7 PUFAs. These compounds are thought to activate PKC through binding on the PS site. One advantage of such esters is that they are generally considered to be more stable that their free acid counterparts.

In at least one embodiment, the PKC-activating fatty acid esters derived from Omega-3 PUFAs are chosen from cyclopropanated eicosapentaenoic acid methyl ester (CP5 form shown below)

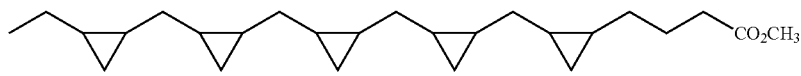 [SMILES: CCC1CC1CC1CC1CC1CC1CC1CC1CC1CC1CCCC(=O)OC]

and cyclopropanated linolenic acid methyl ester (CP3 form shown below).

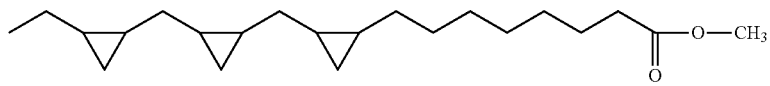 [SMILES: CCC1CC1CC1CC1CC1CC1CCCCCCCC(=O)OC]

In another embodiment, the Omega-3 PUFA esters are chosen from esters of DHA-CP6 and aliphatic and aromatic alcohols. In at least one embodiment, the ester is cyclopropanated docosahexaenoic acid methyl ester (CP6 form shown below).

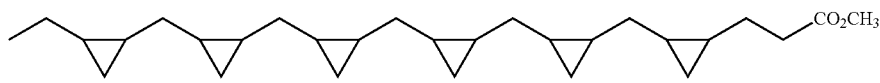 [SMILES: CCC1CC1CC1CC1CC1CC1CC1CC1CC1CC1CC1CC1CCC(=O)OC]

DHA-CP6, in fact, has been shown to be effective at a concentration of 10 nM. See, e.g., U.S Patent Application Publication No. 2010/0022645.

In at least one embodiment, PKC-activating fatty esters derived from Omega-6 PUFAs are chosen from cyclopropanated arachidonic acid methyl ester (CP4 form shown below),

cyclopropanated vernolic acid methyl ester (CP1 form shown below), and

vernolic acid methyl ester (shown below).

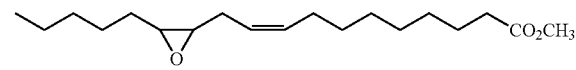

One particularly interesting class of esters are derivatives of DCPLA (CP6-linoleic acid). See, e.g., U.S. Provisional Patent Application No. 61/559,117 and applications claiming priority thereof. In at least one embodiment, the ester of DCPLA is an alkyl ester. The alkyl group of the DCPLA alkyl esters may be linear, branched, and/or cyclic. The alkyl groups may be saturated or unsaturated. When the alkyl group is an unsaturated cyclic alkyl group, the cyclic alkyl group may be aromatic. The alkyl group, In at least one embodiment, may be chosen from methyl, ethyl, propyl (e.g., isopropyl), and butyl (e.g., tert-butyl) esters. DCPLA in the methyl ester form ("DCPLA-ME") is shown below.

In another embodiment, the esters of DCPLA are derived from a benzyl alcohol (unsubstituted benzyl alcohol ester shown below). In yet another embodiment, the esters of DCPLA are derived from aromatic alcohols such as phenols used as antioxidants and natural phenols with pro-learning ability. Some specific examples include estradiol, butylated hydroxytoluene, resveratrol, polyhydroxylated aromatic compounds, and curcumin.

DCPLA-benzyl alcohol ester

Another class of PKC activators is fatty esters derived from cyclopropanated MUFAs. In at least one embodiment, the cyclopropanated MUFA ester is chosen from cyclopropanated elaidic acid methyl ester (shown below),

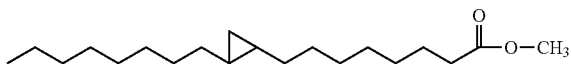 [SMILES: CCCCCCCCC1CC1CCCCCCCC(=O)OC]

and cyclopropanated oleic acid methyl ester (shown below).

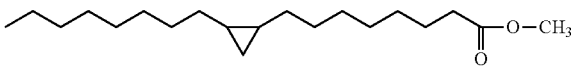 [SMILES: CCCCCCCCC1CC1CCCCCCCC(=O)OC]

Another class of PKC activators is sulfates and phosphates derived from PUFAs, MUFAs, and their derivatives. In at least one embodiment, the sulfate is chosen from DCPLA sulfate and DHA sulfate (CP6 form shown below).

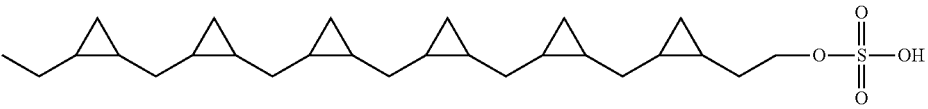 [SMILES: CCC1CC1CC1CC1CC1CC1CC1CC1CC1CC1CC1CC1CCOS(=O)(=O)O]

In at least one embodiment, the phosphate is chosen from DCPLA phosphate and DHA phosphate (CP6 form shown below).

In at least one embodiment the PKC activator is a macrocyclic lactone, bryologs, diacylglcerols, isoprenoids, octylindolactam, gnidimacrin, ingenol, iripallidal, napthalenesulfonamides, diacylglycerol inhibitors, growth factors, polyunsaturated fatty acids, monounsaturated fatty acids, cyclopropanated polyunsaturated fatty acids, cyclopropanated monounsaturated fatty acids, fatty acids alcohols and derivatives, or fatty acid esters.

The PKC activators according to the present disclosure may be administered to a patient/subject in need thereof by conventional methods such as oral, parenteral, transmucosal, intranasal, inhalation, or transdermal administration. Parenteral administration includes intravenous, intra-arteriolar, intramuscular, intradermal, subcutaneous, intraperitoneal, intraventricular, intrathecal, ICV, intracisternal injections or infusions and intracranial administration.

The PKC activators can be compounded into a pharmaceutical composition suitable for administration to a subject using general principles of pharmaceutical compounding. In one aspect, the pharmaceutically acceptable composition comprises a PKC activator and a pharmaceutically acceptable carrier. Thus, the present disclosure relates to a pharmaceutical composition of at least one protein kinase C activator and a carrier.

The formulations of the compositions described herein may be prepared by any suitable method known in the art. In general, such preparatory methods include bringing at least one of active ingredients into association with a carrier. If necessary or desirable, the resultant product can be shaped or packaged into a desired single- or multi-dose unit.

Although the descriptions of compositions provided herein are principally directed to compositions suitable for ethical administration to humans, it will be understood by a skilled artisan that such compositions are generally suitable for administration to animals of all sorts. Modification of pharmaceutical compositions suitable for administration to humans or to render the compositions suitable for administration to various animals is well understood, and the ordinarily skilled veterinary pharmacologist can design and perform such modification with merely ordinary, if any, experimentation. Subjects to which administration of the compositions of the disclosure is contemplated include, but are not limited to, humans and other primates, and other mammals.

As discussed herein, carriers include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other additional ingredients that may be included in the compositions of the disclosure are generally known in the art and may be described, for example, in *Remington's Pharmaceutical Sciences*, Genaro, ed., Mack Publishing Co., Easton, Pa., 1985, and *Remington's Pharmaceutical Sciences*, 20$^{th}$ Ed., Mack Publishing Co. 2000, both incorporated by reference herein.

In at least one embodiment, the carrier is an aqueous or hydrophilic carrier. In a further embodiment, the carrier can be water, saline, or dimethylsulfoxide. In another embodiment, the carrier is a hydrophobic carrier. Hydrophobic carriers include inclusion complexes, dispersions (such as micelles, microemulsions, and emulsions), and liposomes. Exemplary hydrophobic carriers include inclusion complexes, micelles, and liposomes. See, e.g., Remington's: The Science and Practice of Pharmacy 20th ed., ed. Gennaro, Lippincott: Philadelphia, PA 2003, incorporated by reference herein. In addition, other compounds may be included either in the hydrophobic carrier or the solution, e.g., to stabilize the formulation.

The compositions disclosed herein may be administered to a patient in need thereof by any suitable route including oral, parenteral, transmucosal, intranasal, inhalation, or transdermal routes. Parenteral routes include intravenous, intra-arteriolar, intramuscular, intradermal, subcutaneous, intraperitoneal, intraventricular, intrathecal, and intracranial administration. A suitable route of administration may be chosen to permit crossing the blood-brain barrier. See e.g., *J. Lipid Res.* (2001) vol. 42, pp. 678-685, incorporated by reference herein.

In at least one embodiment, the compositions described herein may be formulated in oral dosage forms. For oral administration, the composition may take the form of a tablet or capsule prepared by conventional means with, for example, carriers such as binding agents (e.g., pregelatinized maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods generally known in the art.

In another embodiment, the compositions herein are formulated into a liquid preparation. Such preparations may take the form of, for example, solutions, syrups or suspensions, or they may be presented as a dry product for constitution with water or other suitable vehicle before use. Such liquid preparations may be prepared by conventional means with, for examples, pharmaceutically acceptable carriers such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl p-hydroxybenzoates, or sorbic acid). The preparations may also comprise buffer salts, flavoring, coloring, and sweetening agents as appropriate. In at least one embodiment, the liquid preparation is for oral administration.

In another embodiment of the present disclosure, the compositions herein may be formulated for parenteral administration such as bolus injection or continuous infusion. Formulations for injection may be presented in unit dosage form, e.g., in ampoules, or in multi-dose containers, with an added preservative. The compositions may take such forms as suspensions, solutions, dispersions, or emulsions in oily or aqueous vehicles, and may contain formulary agents such as suspending, stabilizing, and/or dispersing agents.

In another embodiment, the compositions herein may be formulated as depot preparations. Such formulations may be administered by implantation (for example, subcutaneously or intramuscularly) or by intramuscular injection. For example, the compositions may be formulated with a suitable polymeric or hydrophobic material (for example, as an emulsion in an acceptable oil) or ion exchange resin, or as a sparingly soluble derivative, for example, as a sparingly soluble salt.

In another embodiment, at least one PKC activator or combination thereof is delivered in a vesicle, such as a micelle, liposome, or an artificial low-density lipoprotein (LDL) particle. See, e.g., U.S. Pat. No. 7,682,627.

In at least one embodiment, at least one PKC activator or combination of PKC activators may be present in the composition in an amount ranging from about 0.01% to about 100%, from about 0.1% to about 90%, from about 0.1% to about 60%, from about 0.1% to about 30% by weight, or from about 1% to about 10% by weight of the final formulation. In another embodiment, at least one PKC activator or combination of PKC activators may be present in the composition in an amount ranging from about 0.01% to about 100%, from about 0.1% to about 95%, from about 1% to about 90%, from about 5% to about 85%, from about 10% to about 80%, and from about 25% to about 75%.

The present disclosure further relates to kits that may be utilized for administering to a subject a PKC activator according to the present disclosure. The kits may comprise devices for storage and/or administration. For example, the kits may comprise syringe(s), needle(s), needle-less injection device(s), sterile pad(s), swab(s), vial(s), ampoule(s), cartridge(s), bottle(s), and the like. The storage and/or administration devices may be graduated to allow, for example, measuring volumes. In at least one embodiment, the kit comprises at least one PKC activator in a container separate from other components in the system.

The kits may also comprise one or more anesthetics, such as local anesthetics. In at least one embodiment, the anesthetics are in a ready-to-use formulation, for example an injectable formulation (optionally in one or more pre-loaded syringes), or a formulation that may be applied topically. Topical formulations of anesthetics may be in the form of an anesthetic applied to a pad, swab, towelette, disposable napkin, cloth, patch, bandage, gauze, cotton ball, Q-tip™, ointment, cream, gel, paste, liquid, or any other topically applied formulation. Anesthetics for use with the present disclosure may include, but are not limited to lidocaine, marcaine, cocaine, and xylocaine.

The kits may also contain instructions relating to the use of at least one PKC activator or a combination thereof. In another embodiment, the kit may contain instructions relating to procedures for mixing, diluting, or preparing formulations of at least one PKC activator or a combination thereof. The instructions may also contain directions for properly diluting a formulation of at least one PKC activator or a combination thereof in order to obtain a desired pH or range of pHs and/or a desired specific activity and/or protein concentration after mixing but prior to administration. The instructions may also contain dosing information. The instructions may also contain material directed to methods for selecting subjects for treatment with at least one PKC activator or a combination thereof.

The PKC activator can be formulated, alone in suitable dosage unit formulations containing conventional non-toxic pharmaceutically acceptable carriers, adjuvants and vehicles appropriate for each route of administration. Pharmaceutical compositions may further comprise other therapeutically active compounds which are approved for the treatment of neurodegenerative diseases or to reduce the risk of developing a neurodegenerative disorder.

All of the references, patents and printed publications mentioned in the instant disclosure are hereby incorporated by reference in their entirety into this application.

The following examples are provided by way of illustration to further describe certain preferred embodiments of the invention, and are not intended to be limiting of the present disclosure.

EXAMPLES

Mouse studies were performed using bryostatin-1 in accordance with the protocol described below. The following metrics were used to evaluate dosing regimens: induction of brain postsynaptic anchoring protein PSD-95, upregulation of BDNF levels in brain, minimal downregulation of PKC-ε levels, and elevation of brain and plasma concentrations of bryostatin. Groups of 2-3 mice were formed and housed in an approved research animal facility. Water was give ad libitum. A first study involved three groups of mice with animals in each group dosed weekly for 1, 2, 3, or 6 consecutive weeks. Each group had its own control group containing the same number of mice. In this study, mice in the first, second and third groups received an intravenous (i.v.) injection of 10 µg/m$^2$, 15 µg/m$^2$, and 25 µg/m$^2$ dose of bryostatin respectively. For each dose, mice in that group received a single injection of bryostatin weekly for predetermined number of consecutive weeks. Following dosing, mice were sacrificed and the blood and brain of each animal was collected for further analysis.

Figure 2:
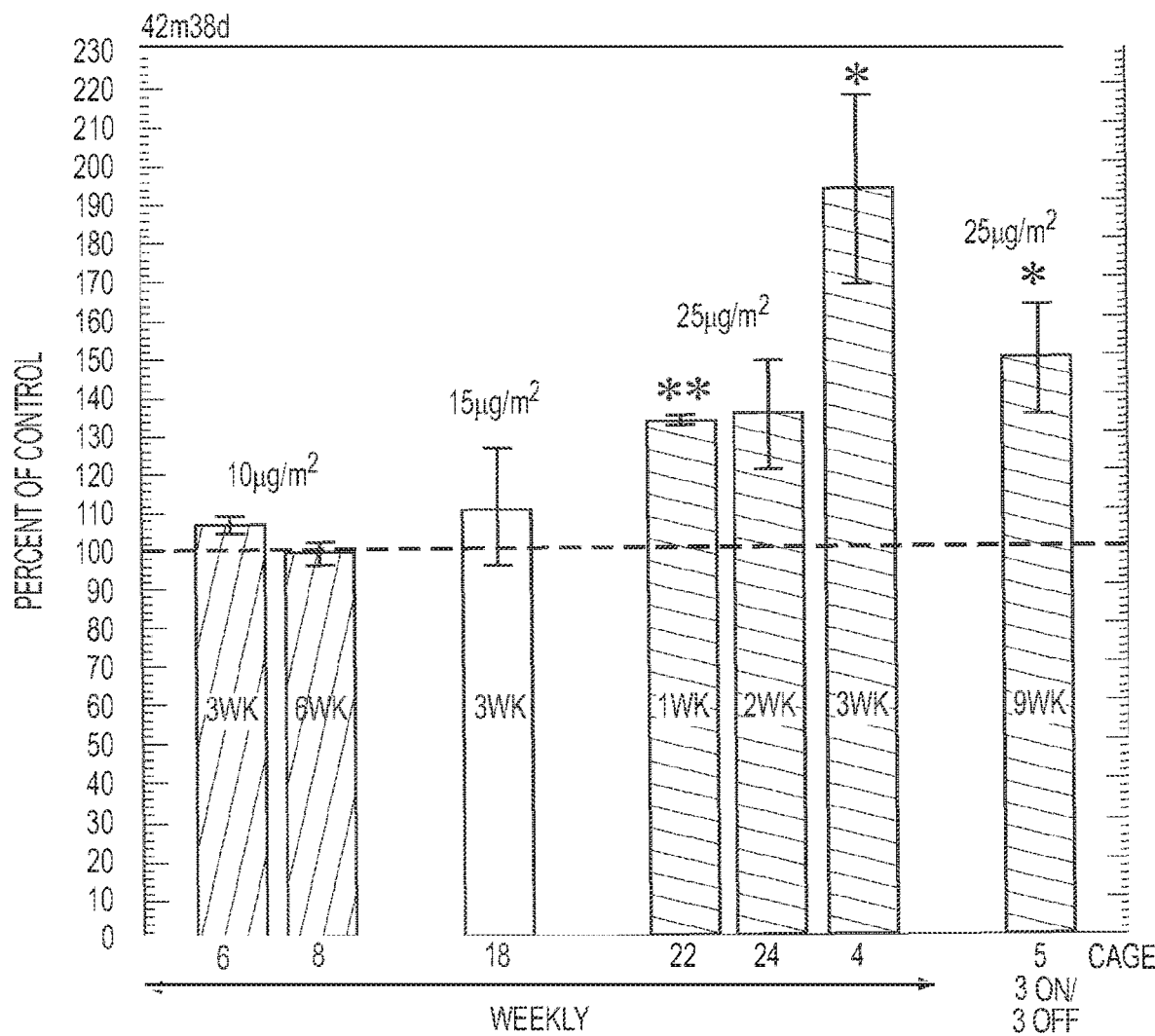
FIG. 2 illustrates the increase in brain BDNF content in mice at 24 hours post intravenous administration of bryostatin. The dose of bryostatin administered is reflected by the number above each bar, while the number within each bar indicates the number of consecutive weeks mice receive a single weekly dose of bryostatin. Control mice were injected with vehicle. BDNF content for each test group was calculated as percent of the corresponding control. BDNF was measured in mouse brain by ELISA 24 h after the last dose. (Mean±SEM, n=3 except Cage 24 n=2, 2-tailed t-test).
Figure 3:
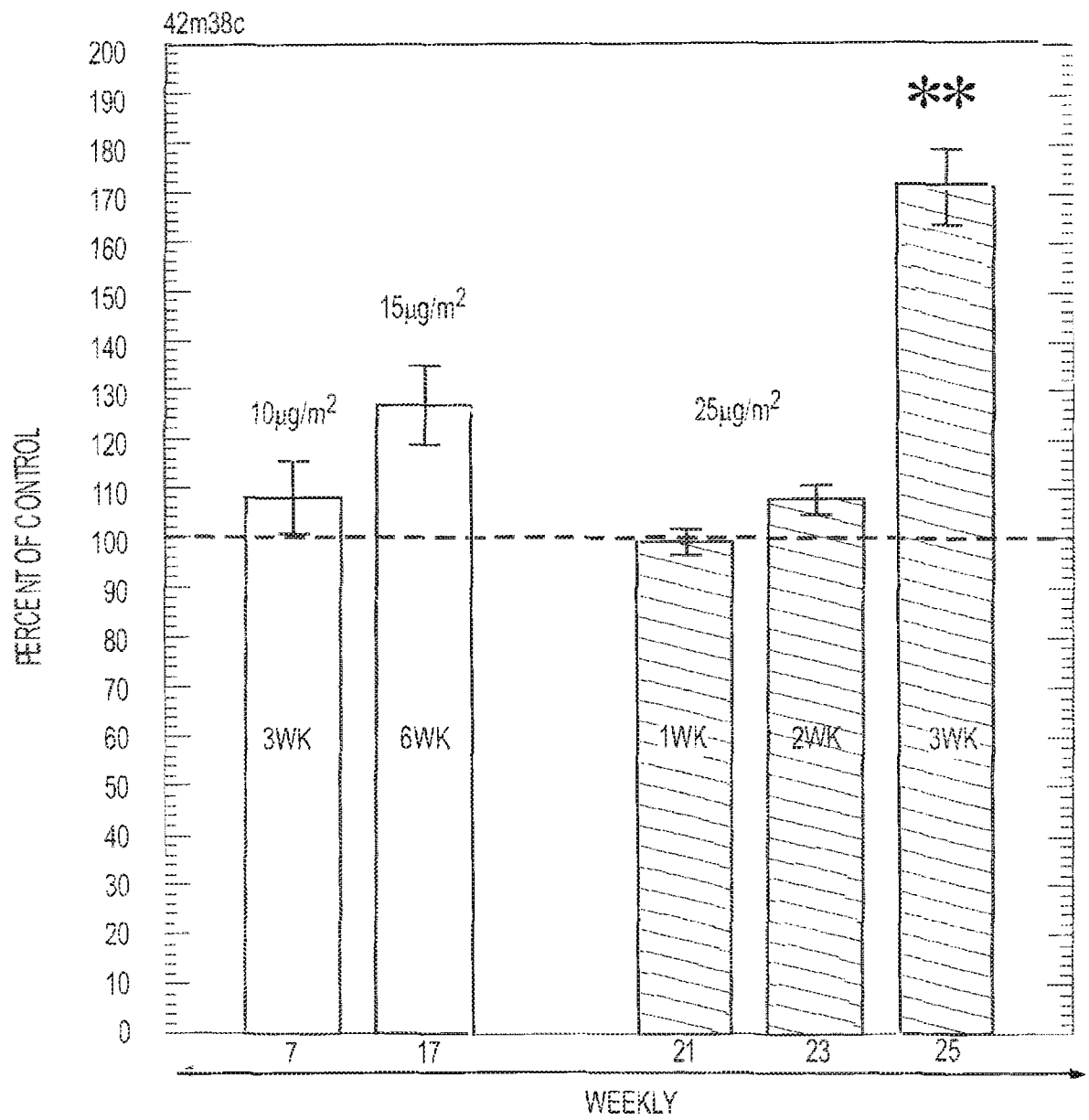
FIG. 3 shows the increase in brain PSD-95 (a marker for postsynaptic density, found only in mature synapses) content in mice at 1 hour post intravenous administration of bryostatin. The dose of bryostatin administered is reflected by the number above each bar, while the number within each bar indicates the number of consecutive weeks mice receive a single weekly dose of bryostatin. Control mice were injected with vehicle. PSD-95 was measured in mouse brain by Western Blot 1 h after the last dose. (Mean±SEM, n=3 except Cage 23 n=2, 2-tailed t-test).
Figure 4A:
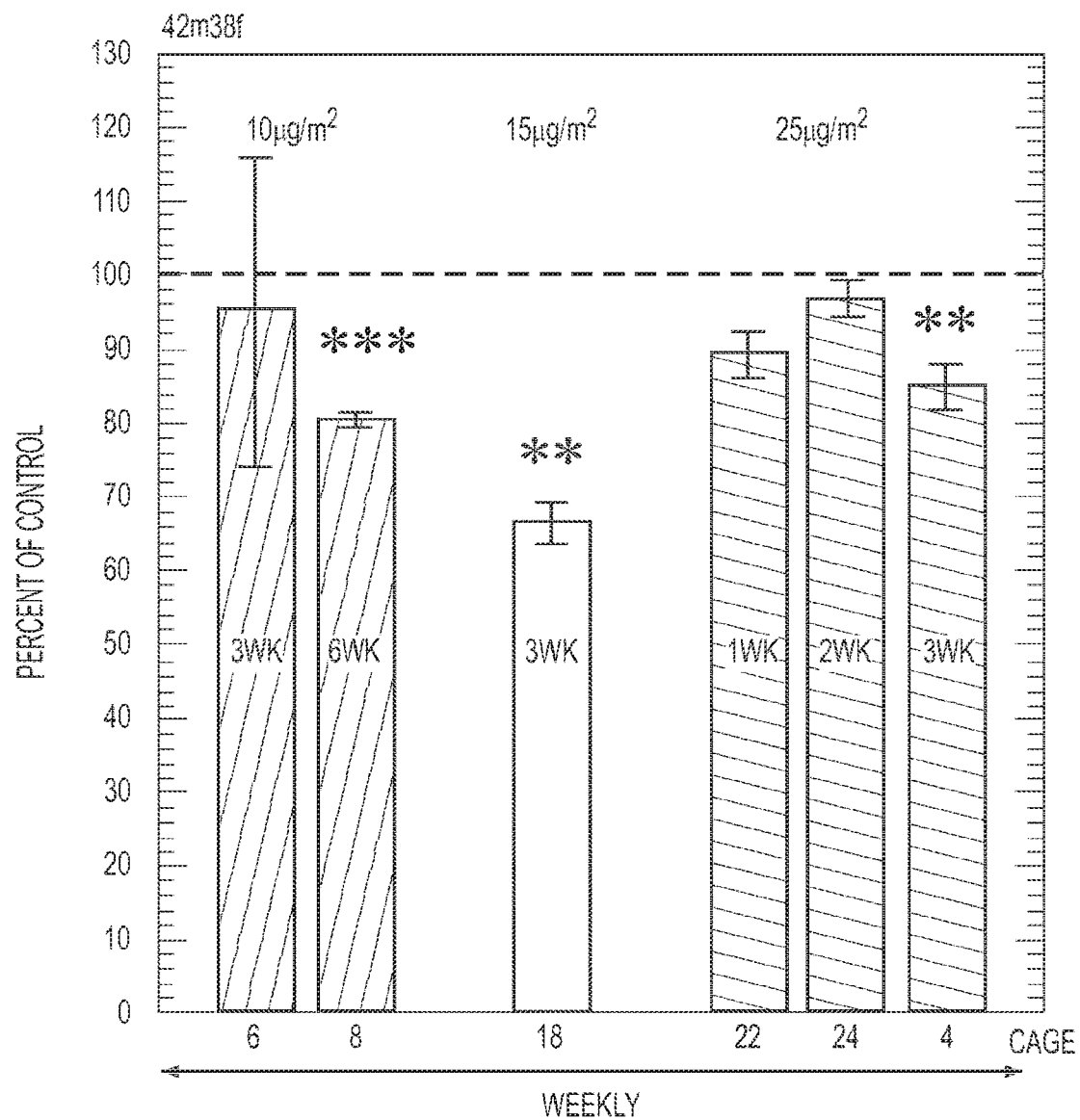
FIGS. 4A-4B illustrate the downregulation of PKCε in the brain mice at 24 hours post intravenous administration of bryostatin. (A) Downregulation of brain PKCε in mice after intravenous administration of bryostatin at doses of 10 μg/m², 15 μg/m², and 25 μg/m² for 1-6 consecutive weeks. (B) Downregulation of brain PKCε in mice after intravenous administration of bryostatin at two different doses (i) 2×25+20 μg/m², and (ii) 25 μg/m². Dosing regimen is disclosed along the abscissa.

FIGS. 2, 3, and 4A illustrate the results of this study. FIG. 2 illustrates the increase in brain BDNF levels in mice receiving 10 µg/m$^2$, 15 µg/m$^2$, and 25 µg/m$^2$ bryostatin for 1, 2, 3, and 6 consecutive weeks. The dotted horizontal line in FIG. 2 illustrates the BDNF levels in the brain of control mice that received i.v. injections of the vehicle. A dose of 10 µg/m$^2$, (i.v. administration) of bryostatin for 3 or 6 consecutive weeks did not result in elevated levels of brain BDNF. While some increase in the levels of brain BDNF was observed at a dose of 15 µg/m$^2$ for three consecutive weeks, the maximum increase in brain BDNF levels was seen at a dose of 25 µg/m$^2$. At a dose of 25 µg/m$^2$, the levels of brain BDNF increased with each successive week of dosing, that is, brain BDNF levels were greatest after three consecutive weeks of dosing.

A similar observation was made concerning the levels of the synaptogenesis marker PSD-95. Brain and blood samples of study subjects showed higher amounts of PSD-95 after three weeks at a dose of 25 µg/m$^2$ bryostatin, administered i.v. as a once per week injection. See FIG. 3. In addition, as shown in FIG. 4A, 25 µg/m$^2$ administered in three consecutive weekly doses did not produce more PKC-ε downregulation in brain than did three consecutive weeks of lower doses. Continued weekly dosing at 10 µg/m$^2$ for another three consecutive weeks (total of 6 consecutive weeks) appeared to result in downregulation. See FIG. 4A.

Figure 4B:
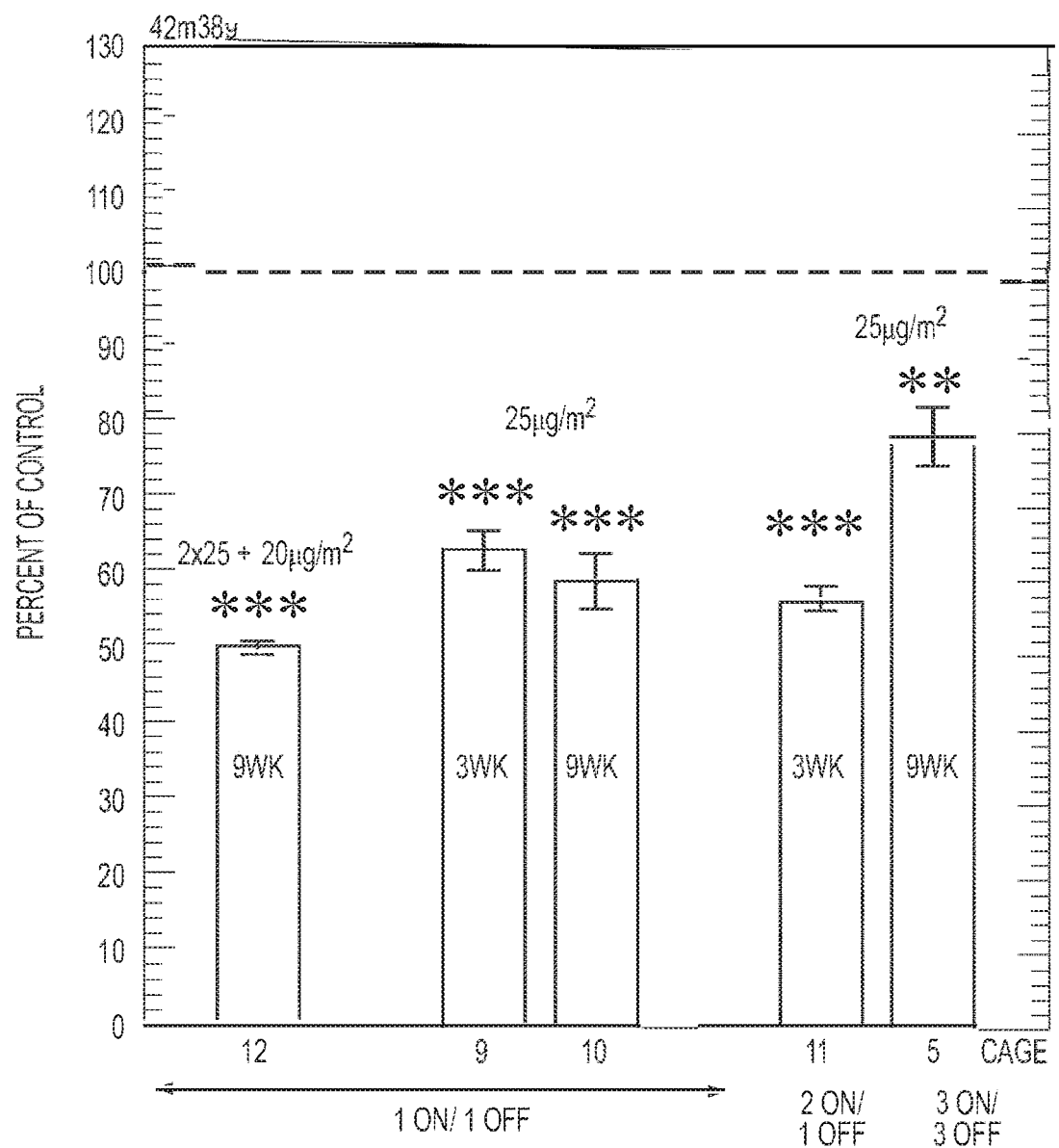

Although 25 µg/m$^2$ administered in three consecutive weekly doses did not produce more PKC-ε downregulation in brain than did three consecutive weeks of lower doses (see FIG. 4A), with continued dosing at this higher level additional downregulation occurred as shown in FIG. 4B for the "1 on/1 off" and "2 on/1 off" regimens. Since PKC-ε is the biological target of bryostatin, lower levels of this protein may be responsible for the decline in cognitive benefits observed in the AD patients that were part of the Compassionate Use study described above. (See FIG. 1 where decline in psychometric scores closely tracked the decline in PCK-ε levels). In particular, FIG. 4B shows, inter alia, the results from a group of mice dosed weekly with bryostatin at 25 µg/m$^2$ for three consecutive weeks, followed by cessation of drug administration for three consecutive weeks, and then a second round of dosing at 25 µg/m$^2$ for an additional three consecutive weeks (that is, a "3 on/3 off/3 on" dosing regimen). FIG. 4B also shows the results for mice dosed at 25 µg/m$^2$ at a "1 on/1 off" regimen for a total of nine weeks (i.e., one dose of bryostatin on weeks 1, 3, 5, 7, and 9, with no dosing in weeks 2, 4, 6, and 8). FIG. 4B additionally shows the results for mice dosed at 25 µg/m$^2$ for another regimen starting with "2 on/1 off" immediately followed by alternating "1 on/1 off" until reaching the ninth total week (i.e., one dose of bryostatin on weeks 1, 2, 4, 6, 8, with no dosing in weeks 3, 5, 7, and 9).

As shown in FIG. 4B, increasing the duration of the rest intervals (i.e., "off" intervals) to three weeks significantly reduced PKC downregulation. That is, the "3 on/3 off" dosing regimen increased brain PKC-ε levels in mice over the other regimens tested, and thus produces optimal cognitive benefits.

FIG. 2 shows that brain BDNF in mice reached its highest level after three consecutive weekly doses of bryostatin at 25 µg/m$^2$ and remained elevated after three additional consecutive weeks of no dosing, followed by three more consecutive weekly doses at 25 µg/m$^2$. Since BDNF is a peptide that induces synaptogenesis (i.e., the formation of new synapses), a "3 on/3 off" regimen maximizes synaptogenesis and minimizes PKC downregulation.

Figure 5:
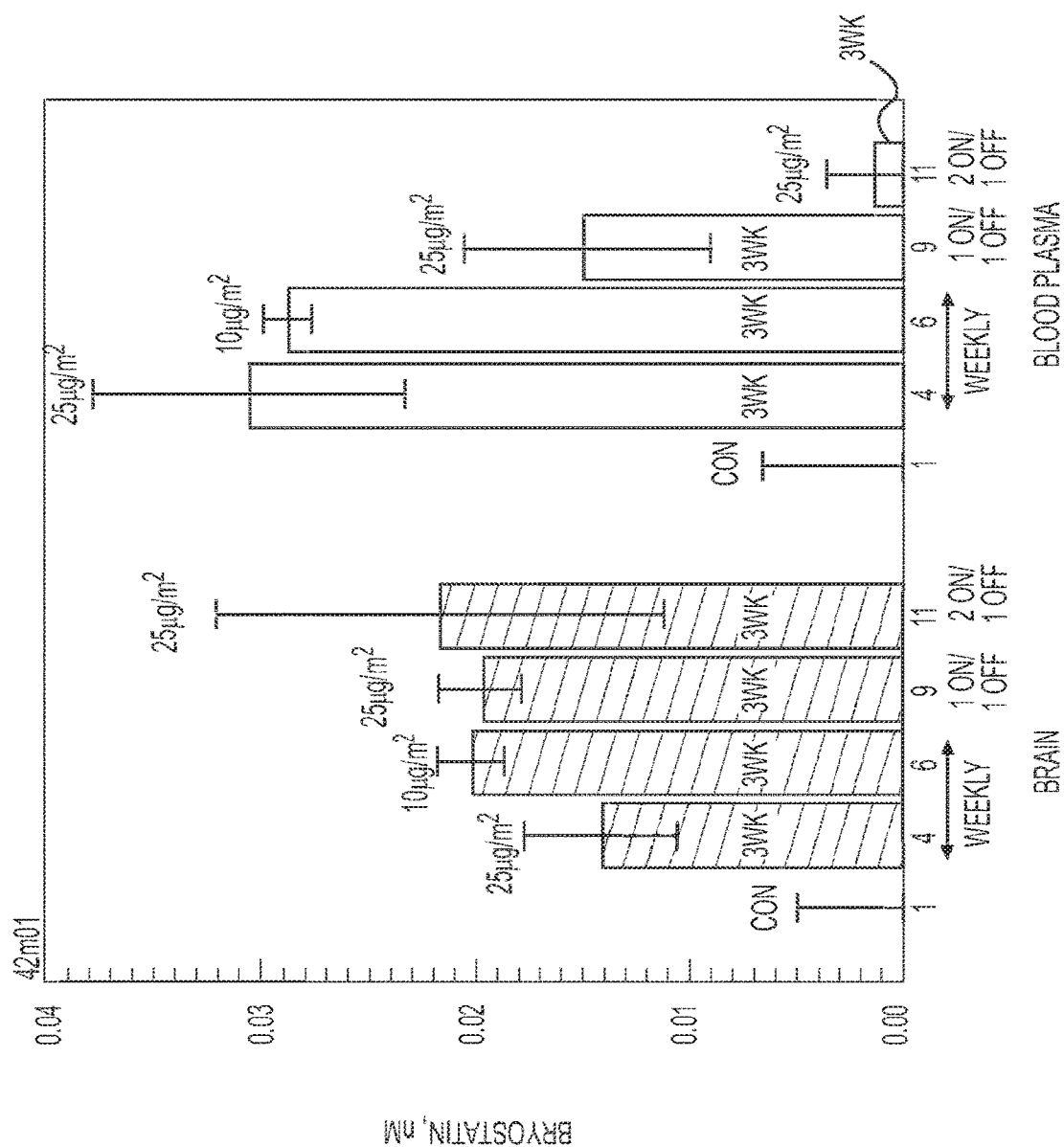
FIG. 5 illustrates the steady state concentration of bryostatin in the brain and plasma of mice following intravenous administration at the indicated doses.

Further evaluation was performed on bryostatin crossing the blood-brain-barrier (BBB) and the steady state levels of bryostatin in the brain and plasma of mice. FIG. 5 shows the results of the study. Bryostatin administered intravenously crossed the BBB. The concentration of bryostatin in mice brain was less than its concentration in plasma. However, as FIG. 5 illustrates, the concentration in brain was no less than two-fold lower than the plasma concentrations for comparable doses under steady-state conditions.

A weekly dosing regimen of a single injection of bryostatin at a dose of 25 µg/m$^2$ for three consecutive weeks was less effective at increasing bryostatin concentration in mice brain than a "1 on/1 off" or a "2 on/1 off" administration of the 25 µg/m$^2$ dose. In contrast, plasma concentrations of bryostatin were greater when the drug was administered as a single injection for three consecutive weeks. Blood plasma concentrations of bryostatin were less in mice receiving a 25 µg/m$^2$ dose as a "1 on/1 off" or a "2 on/1 off" administration. Without being bound to a specific theory, it is hypothesized that the intermittent dosing regimen facilitates the transport of bryostatin across the BBB.

A. General Procedures

Western Blot Analysis

Cells were harvested in homogenizing buffer containing 10 mM Tris-Cl (pH 7.4), 1 mM PMSF (phenylmethylsulfonyl fluoride), 1 mM EGTA, 1 mM EDTA, 50 mM NaF, and 20 µM leupeptin and were lysed by sonication. The homogenate was centrifuged at 100,000×g for 15 min at 4° C. to obtain the cytosolic fraction (supernatant) and membrane (pellet). The pellet was resuspended in the homogenizing buffer by sonication. Protein concentration was measured using the Coomassie Plus (Bradford) Protein Assay kit (Pierce, USA). Following quantification, 20 µg of protein from each sample was subjected to SDS-PAGE analysis in 4-20% gradient Tris-Glycine gel (Invitrogen, USA). The separated protein was then transferred to nitrocellulose membrane. The membrane was blocked with BSA at room temperature for 15 min and was incubated with primary antibody over night at 4° C. After the incubation, it was washed three times with TBS-T (Tris Buffered saline-Tween 20) and further incubated with alkaline phosphatase conjugated secondary antibody (Jackson Immunoresearch Laboratories, USA) at 1:10,000 dilution for 45 min. The membrane was finally washed three times with TBS-T and developed using the 1-step NBT-BCIP substrate (Pierce, USA). Western Blot was imaged in the ImageQuant RT-ECL (GE Life Sciences, Piscataway, NJ) and densitometric quantification was performed using the IMAL software (Blanchette Rockefeller Neurosciences Institute, Morgantown, WV). For translocation assays, PKC activation was represented as the percentage of total protein in the membrane (membrane/cytosol+membrane).

PKC Assay

To measure PKC activity, 10 µg of protein from either cytosol or membrane was incubated for 15 min at 37° C. in the presence of 10 µM histones, 4.89 mM CaCl$_2$, 1.2 µg/µl phosphatidyl-L-serine, 0.18 µg/µl 1,2-dioctanoyl-sn-glycerol, 10 mM MgCl$_2$, 20 mM HEPES (pH 7.4), 0.8 mM EDTA, 4 mM EGTA, 4% glycerol, 8 µg/ml aprotinin, 8

µg/ml leupeptin, 2 mM benzamidine, and 0.5 µCi of [γ-$^{32}$P] ATP. [$^{32}$P]Phosphoprotein formation was measured by adsorption onto phosphocellulose as described previously. See Nelson et al. (2009) *J Biol Chem* 284, 34514-34521.

Cell Viability Assay

Viability of cells was measured by MTT assay. MTT (3-(4,5-Dimethylthiazol-2-yl)-2,5-diphenyltetrazolium bromide) is a tetrazolium salt that is cleaved to formazan by the succinate dehydrogenase, which is only active in viable cells. After solubilization of the formazan, the amount of dye can be quantified with a microplate reader at 570 nm along with a reference of 630 nm. For MTT assay, $5 \times 10^4$ neurons from mice brains were plated on each well of 24-well plates coated with poly-D-lysine. After treatment, the cells were washed with 1xPBS and were incubated with 200 µl of 1 mg/ml MTT solution (Sigma, USA) at 37° C. for 2 hr. Then the MTT-solution was removed and the cells were lysed with 200 µl isopropanol containing 0.04 M HCl and 160 mM NaOH for 10 min. Finally, the reading was done at 570 nm and 630 nm. All the samples were done in triplicates and the data was represented as the percentage of control.

Statistical Analysis

All experiments were performed at least in triplicate, as noted in the figure legends. For confocal images, six or more random fields from three independent experiments were considered for analysis. Data are presented as mean±SEM. All data were analyzed by one-way ANOVA and Newman-Keuls multiple-comparison post-test. Significantly different groups were further analyzed by Student's t test using GraphPad Prism 6 software. p-values<0.05 were considered statistically significant.

B. Preclinical Studies

C57BL/6 male mice weighing between 19-21 grams were obtained from Charles River and housed in cages, 1 mouse/cage in a vivarium at the Blanchette Rockefeller Neurosciences Institute. Animals were allowed access to water ad libitum.

In these studies, bryostatin was administered intravenously (i.v.) by injection into the tail vein of a mouse. Stock solutions of bryostatin were prepared in dimethyl sulfoxide (DMSO). Prior to administration to a mouse, the stock DMSO solution of bryostatin was diluted to a predetermined concentration by dilution with phosphate buffered saline/saline (PBS/saline).

Three different dosing regimens (injection schedules) were compared. The dosing regimens tested were weekly dosing, dosing every other week (alternating weeks), and spaced or intermittent dosing. Table 1 describes the injection schedule

TABLE 1

| Dosing Regimen | Experimental Details |
| --- | --- |
| Weekly - One injection per week, every week | Mice were injected i.v. with Bryostatin at 10, 15, or 25 µg/m² once per week for up to 6. |
| Alternating - One injection every other week | Mice were injected i.v. with Bryostatin at 25 µg/m² every other week for up to 9 weeks. |
| Spaced - One injection per week for 3 weeks, 3 weeks off | Mice were injected i.v. with Bryostatin at 25 µg/m² once per week for 3 consecutive weeks (on) followed by no dosing for 3 weeks (off), and a second round of dosing for 3 weeks for a total of 9 weeks. |

The brain, whole blood, and plasma of mice in each dosing group as well as control mice was collected at 1 hour, 24 hours and 7 days after the last injection of bryostatin. PBMC's were isolated from blood and the brain, blood, plasma and PBMC's were frozen immediately using dry ice. Prior to analysis PBMC's were counted by diluting the sample (10 µl aliquot), 10-fold and the PBMC's counted using a Millipore Scepter cell counter. Every group of test animals had its own control group (N=3). Mice in the control group were injected with vehicle at a frequency similar to the dosing regimen and these animals were sacrificed and tested in parallel with mice in the test group.

PKC activity in brain and PBMC's was measured using a $^{32}$P assay within 24 hours of collection of blood or by ELISA. Standard techniques known in the art for ELISA are described in *Methods in Immunodiagnosis*, 2$^{nd}$ Edition, Rose and Bigazzi, eds., John Wiley and Sons, New York 1980 and Campbell et al., *Methods of Immunology*, W. A. Benjamin, Inc., 1964, both of which are incorporated herein by reference. Such assays may be direct, indirect, competitive, or noncompetitive immunoassays as described in the art (In "Principles and Practice of Immunoassay" (1991) Christopher P. Price and David J. Neoman (eds), Stockton Press, NY, NY; Oellirich, M. 1984. *J. Clin. Chem. Clin. Biochem.* 22: 895-904 Ausubel, et al. (eds) 1987 in *Current Protocols in Molecular Biology*, John Wiley and Sons, New York, New York.

Each measurement was performed four times (x4). BDNF levels were measured using ELISA and the concentration of protein PSD-95 was measured by Western Blot. High performance liquid chromatography-mass spectral analysis was used to measure the concentration of bryostatin in blood and brain samples based on a standard curve. Total protein concentrations were measured Coomassie Plus (Bradford) Protein Assay kit.

Table 2 illustrates the dosing schedule of mice receiving weekly injections of bryostatin. In this study, mice were administered 10 µg/m², 15 µg/m², and 25 µg/m² dose of bryostatin as a single injection once per week for the indicated number of consecutive weeks. Blood and brain tissue were collected at the end of dosing and the concentrations of BDNF, PSD-95 and PKC-ε in plasma, PBMC's and brain were determined as described above.

TABLE 2

| Bryostatin Injections - One Injection/Week, Every Week 4 | | | | | | | | | Dose | Delay | |
| --- | --- | --- | --- | --- | --- | --- | --- | --- | --- | --- | --- |
| 1 | 2 | 3 | 4 | 5 | 6 | 7 | 8 | 9 | µg/m² | (h) | Cage |
| ✓x | | | | | | | | | 25 | 1 | 21 |
| ✓ | ✓x | | | | | | | | 25 | 1 | 23 |
| ✓ | ✓x | | | | | | | | 25 | 24 | 24 |
| ✓ | ✓ | ✓x | | | | | | | 10 | 24 | 6 |
| ✓ | ✓ | ✓x | | | | | | | 15 | 1 | 17 |
| ✓ | ✓ | ✓x | | | | | | | 15 | 24 | 18 |
| ✓ | ✓ | ✓x | | | | | | | 25 | 1 | 25 |
| ✓ | ✓ | ✓x | | | | | | | 25 | 24 | 4 |

TABLE 2-continued

| Bryostatin Injections - One Injection/Week, Every Week 4 | | | | | | | | | Dose μg/m² | Delay (h) | Cage |
|---|---|---|---|---|---|---|---|---|---|---|---|
| 1 | 2 | 3 | 4 | 5 | 6 | 7 | 8 | 9 | | | |
| ✓ | ✓ | ✓ | ✓ | ✓ | ✓x | | | | 10 | 1 | 7 |
| ✓ | ✓ | ✓ | ✓ | ✓ | ✓x | | | | 10 | 24 | 8 |

✓ = injection;
✓x = injection + collection of blood and brain.

Table 3 illustrates the dosing schedule of mice receiving alternating, or spaced (intermittent) injections of bryostatin.

TABLE 3

| Alternating Bryostatin Injections - One Injection Every Other Week | | | | | | | | | Dose μg/m² | Delay | Cage |
|---|---|---|---|---|---|---|---|---|---|---|---|
| 1 | 2 | 3 | 4 | 5 | 6 | 7 | 8 | 9 | | | |
| ✓ | ✓x | | | | | | | | 25 | 24 h | 9 |
| ✓ | | ✓ | | ✓ | | ✓ | ✓x | | 25 | 24 h | 10 |
| ✓ | ✓ | | ✓ | | ✓ | | ✓ | x | 25/20 | 7 d | 12 |

| Spaced Bryostatin Injections - One Injection/Week, then 1-3 Weeks Off | | | | | | | | | Dose μg/m² | Delay | |
|---|---|---|---|---|---|---|---|---|---|---|---|
| ✓ | ✓ | x | | | | | | | 25 | 7 d | 11 |
| ✓ | ✓ | ✓ | | | | ✓ | ✓ | ✓x | 25 | 24 h | 5 |

✓ = injection;
x = collection of blood and brain;
✓x = injection + collection of blood and brain.

1. Effect of Dose and Dosing Regimen on BDNF Levels

As mentioned above, the effect of dosing regimen on enhancement of cognitive ability was evaluated. Brain-derived neurotrophic factor PSD-95, PKC-ε, and the extent of translocation of PKC-ε from the cytosol to the membrane of a neuron are well known metrics for evaluating improvement of cognitive function or cognitive ability. Table 4 illustrates that bryostatin increased the levels of BDNF and this increase correlated directly with the number of consecutive weeks over which dosing was carried out. For example, at a dose of 25 μg/m², greater levels of BDNF were measured in the brains of mice receiving a weekly dose of bryostatin for 3 consecutive weeks than mice receiving a weekly dose of bryostatin for 2 consecutive weeks. See data related to cages 4 and 24 respectively. The level of BDNF in brain also correlated with the dose of bryostatin. As Table 4 shows, increasing the dose of bryostatin elevated levels of BDNF in mice.

TABLE 4

| Cage | BDNF (% of Control) | SEM | P-Value |
|---|---|---|---|
| 6 | 107.047 | 2.2147 | 0.20 |
| 8 | 99.137 | 2.6599 | 0.93 |
| 18 | 110.969 | 15.1371 | 0.57 |
| 22 | 133.142 | 0.9038 | 0.002 |
| 24 | 135.095 | 13.7027 | 0.066 |
| 4 | 192.869 | 24.3289 | 0.02 |
| 5 | 149.023 | 14.3585 | 0.045 |

2. Effect of Dose and Dosing Regimen on PSD-95 Levels

A similar trend was observed for the PSD-95 protein levels in mice. PSD-95 is a marker for synaptogenesis and an increase in the concentration of this marker in brain is believed to correlate to enhancements or improvements of cognitive abilities. Table 5 illustrates that treatment with bryostatin increased PSD-95 concentrations. The observed increase in concentration correlates to the dose administered and the dosing regimen used. For example, increasing doses of 10 μg/m² (cage 7, Table 5), 15 μg/m² (cage 17), and 25 μg/m² (cages 21, 23 and 25), resulted in an increase in the concentration of PSD-95 in a dose dependent manner. The number of consecutive weeks the dose was administered also influenced PSD-95 concentrations. At the 25 μg/m² dose, mice in cage 21 were dosed for 1 week, while mice in cages 23 and 25 were dosed for 2 and 3 consecutive weeks respectively. Table 5 shows that PSD-95 concentration increases as the number of consecutive weeks over which the 25 μg/m² dose of bryostatin increases.

TABLE 5

| Cage | PSD-95 (% of Control) | SEM | P-Value |
|---|---|---|---|
| 7 | 108.176 | 7.56388 | 1.0 |
| 17 | 126.969 | 8.08476 | 0.0110 |
| 21 | 99.453 | 2.50088 | 0.160 |
| 23 | 107.570 | 2.77821 | 0.072 |
| 25 | 171.203 | 7.75988 | 0.006 |

PSD-95 was measured by Western Blot 1 h after the last dose;
Mean ± SEM,
n = 3 except Cage 23 n = 2,
2-tailed t-test 3. Effect of Dose and Dosing Regimen on PKC-ε Levels Tables 6 and 7 show the effect of dosing regimen on total PKC levels in mice. The data in Table 6 were obtained from a mouse study in the animals received the specified dose of bryostatin as a single weekly injection for 1-3 consecutive weeks. In Table 6, mice in cages 6 and 8 received a weekly injection of 10 μg/m² bryostatin for 3 weeks or 6 weeks respectively. Mice in cage 18 received 15 μg/m² bryostatin as a weekly injection for 3 weeks and mice in cages 24 and 4 received a 25 μg/m² bryostatin as a weekly injection for 2 weeks and 3 weeks respectively.

TABLE 6

| Cage | PKC (% of Control) | SEM | P-Value |
| --- | --- | --- | --- |
| 6 | 95.197 | 20.7878 | 0.82 |
| 8 | 80.441 | 0.8886 | 5e−05 |
| 18 | 66.430 | 2.9300 | 0.0026 |
| 22 | 89.206 | 2.9643 | 0.08 |
| 24 | 96.723 | 2.4507 | 0.51 |
| 4 | 84.841 | 2.9789 | 0.0072 |

Table 7 illustrates the effect of an alternating dosing regimen (cages 9, 10), and an intermittent or sporadic dosing regimen (cages 5, 11 and 12) on the total PKC levels in mice. Each group of mice in Table 7, received 25 μg/m² bryostatin, administered as a once a week injection. From Table 7 it is evident that the 3on/3off/3on spaced (intermittent) dosing regimen showed maximal effect in preventing and/or reducing the down-regulation of PKC (cage 5). The PKC level for mice in cage 5 are almost double the PKC level for mice in cage 12 where a 2on/1off/1on/1off/1on/1off/2on dosing regimen was tested. The 3on/3off/3on spaced dosing regimen was more effective at preventing and/or reducing the down-regulation of PKC that a 9 week alternating dosing regimen administered to mice in cage 10.

TABLE 7

| Cage | PKC (% of Control) | SEM | P-Value |
| --- | --- | --- | --- |
| 12 | 49.924067 | 0.44507 | 0.00026 |
| 09 | 63.018549 | 2.85218 | 0.0002 |
| 10 | 59.113528 | 3.69247 | 0.00057 |
| 11 | 56.7 | 1.59643 | 5.27e−07 |
| 05 | 78.200753 | 4.02924 | 0.0078 |

The PKC translocation ratio, that is, the amount of PKC translocated to the membrane to the amount of PKC in cytosol was determined for different doses of bryostatin and the number of consecutive weeks over which each dosing was carried out. This ratio is shown below in Table 8, where mice in cage 7 were administered 10 μg/m² bryostatin for 6 consecutive weeks, mice in cage 17 were administered 15 μg/m² bryostatin for 3 consecutive weeks, and mice in cages 21, 23, and 25 were administered 25 μg/m² bryostatin for 1, 2, and 3 consecutive weeks respectively.

TABLE 8

| Cage | PKC (% of Control) | SEM | P-Value |
| --- | --- | --- | --- |
| 7 | 100.121 | 1.21065 | 0.96 |
| 17 | 108.464 | 2.04427 | 0.0197 |
| 21 | 109.653 | 0.51480 | 0.150 |
| 23 | 102.057 | 0.86264 | 0.16 |
| 25 | 93.815 | 2.53906 | 0.084 |

4. Effect of Dosing Regimen on Brain and Plasma Bryostatin Levels

The therapeutic efficacy of bryostatin depends at least in part on its ability to cross the blood-brain-barrier (BBB). To evaluate whether dosing regimen influences the bryostatin levels in brain, mice were administered the drug intravenously. Table 9 illustrates the effect of dose and dosing regimen on bryostatin levels in the brain and plasma of mice. Sporadic dosing increased the levels of bryostatin in brain compared to plasma. See data for mice in cages 9 and 11.

TABLE 9

| Cage | bryostatin (% of Control) | SEM |
| --- | --- | --- |
| BRAIN | | |
| 1 | 0.0000 | 0.0048 |
| 4 | 0.0140 | 0.0035 |
| 6 | 0.0202 | 0.0015 |
| 9 | 0.0197 | 0.0020 |
| 11 | 0.0217 | 0.0105 |
| PLASMA | | |
| 1 | 0.0000 | 0.0065 |
| 4 | 0.0306 | 0.0073 |
| 6 | 0.0287 | 0.0011 |
| 9 | 0.0148 | 0.0058 |
| 11 | 0.0012 | 0.0024 |

What is claimed is:

1. A method for treating Alzheimer's disease in a subject, the method comprising administering to said subject a bryostatin compound by an intermittent dosing regimen in which the subject is administered a dosage of about 10 to about 40 μg/m² once a week for at least two consecutive weeks followed by at least one week of no administration of the bryostatin compound followed by administration of about 10 to about 40 μg/m² once a week for at least two consecutive weeks.

2. The method of claim 1, wherein the bryostatin compound is bryostatin-1.

3. The method of claim 1, wherein the bryostatin compound is administered intravenously.

4. The method of claim 1, wherein the bryostatin compound is administered as an oral dosage form.

5. The method of claim 1, wherein the subject has early stage Alzheimer's disease.

6. The method of claim 1, wherein said dosage is about 10 to about 40 μg/m².

7. The method of claim 1, wherein said dosage is about 15 to about 30 μg/m².

* * * * *